US005487979A

United States Patent [19]
DiFiore et al.

[11] Patent Number: 5,487,979
[45] Date of Patent: Jan. 30, 1996

[54] DNA ENCODING HUMAN AND MURINE EPS15, A SUBSTRATE FOR THE EPIDERMAL GROWTH FACTOR RECEPTOR

[75] Inventors: Pier P. DiFiore, Bethesda, Md.; Francesca Fazioli, Ancona, Italy

[73] Assignee: The United States of America as represented by the Department of Health and Human Services, Washinton, D.C.

[21] Appl. No.: 95,737

[22] Filed: Jul. 22, 1993

Related U.S. Application Data

[63] Continuation-in-part of Ser. No. 935,311, Aug. 25, 1992, Pat. No. 5,378,809.

[51] Int. Cl.$^6$ ............................. C12N 1/21; C12N 5/10; C12N 15/12; C12N 15/63

[52] U.S. Cl. .................................... 435/240.2; 435/252.3; 435/320.1; 536/23.5

[58] Field of Search ................................ 536/23.5, 24.5; 435/320.1, 240.2, 252.3

[56] References Cited

PUBLICATIONS

Barnard et al., Oncogene 9:1039–1045 (1994).
Wong et al., Oncogene 9:1591–1597 (1994).
Helene, Anti–Cancer Drug Design 6:569–584 (1991).
Aaronson, Stuart A. (1991) "Growth Factors and Cancer" *Science* 254:1146–1153.
Bairoch, Amos (1992) "Prosite: a dictionary of sites and patterns in proteins" *Nucleic Acids Res.* 20:2013–2018.
Coughlin, Shaun R. et al. (1989) "Role of phosphatidylinositol kinase in PDGF receptor signal transduction" *Science* 243:1191–1194.
DiFiore, Pier P. et al. (1987) "Overexpression of the human EGF receptor confers an EGF–dependent transformed phenotype to NIH 3T3 cells" *Cell* 51:1063–1070.
DiFiore, Pier P. et al. (1990) "The carboxy–terminal domains of erbB–2 and epidermal growth factor receptor exert different regulatory effects on intrinsic receptor tyrosine kinase function and transforming activity" *Mol. Cell. Biol.* 10:2749–2756.
DiFiore, Pier P. et al. (1990) "EGF receptor and erbB–2 tyrosine kinase domains confer cell specificity for mitogenic signaling" *Science* 248:79–83.
Escobedo, Jaime A. et al. (1991) "cDNA cloning of a novel 85 kd protein that has SH2 domains and regulates binding of P13–kinase to the PDGF β–receptor" *Cell* 65:75–82.
Fazioli, F. et al. (1992) "Identification and biochemical characterization of novel putative substrates for the epidermal growth factor receptor kinase*" *J. Biol. Chem.* 267:5155–5161.
Fazioli, F. et al. (1991) "The erbB–2 mitogenic signaling pathway: Tyrosine phosphorylation of phospholipase C–γ and GTPase–activating protein does not correlate with erbB–2 mitogenic potency" *Mol. Cell. Biol.* 11:2040–2048.
Fazioli, F. et al. (1993) "The ezrin–like family of tyrosine kinase substrates: receptor-specific pattern of tyrosine phosphorylation and relationship to malignant transformation" *Oncogene* 8:1335–1345.
Felgner, P. L. et al. (1991) "Gene therapeutics" *Nature* 349:351–352.
Giard, Donald J. et al. (1973) "In vitro cultivation of human tumors: Establishment of cell lines derived from a series of solid tumors" *J. Nat'l Cancer Institute* 51:1417–1423.
Gould, Kathleen L. et al. (1988) "Platelet–derived growth factor induces multisite posphorylation of pp60$^{c-src}$ and increases its protein–tyrosine kinase activity" *Mol. Cell. Bio.* 8:3345–3356.
Green, Pamela J. et al. (1986) "The role of antisense RNA in gene regulation" *Ann. Rev. Biochem.* 55:569–597.
Griffin, Linda C. et al. (1989) "Recognition of thymine–adenine base pairs by guanine in a pyrimidine triple helix motif" *Science* 245:967–971.
Heizmann et al. (1991) "Intracellular calcium–binding proteins: more sites than insights" *Trends Biochem. Sci.* 16:98–103.
Hunter, Tony (1982) "Synthetic peptide substrates for a tyrosine protein kinase*" *J. Bio. Chem.* 257:4843–4848.
Kaplan, David R. et al. (1990) "PDGF β–receptor stimulates tyrosine phosphorylation of GAP and association of GAP with a signaling complex" *Cell* 61:125–133.
Kazlauskas, Andrius et al. (1989) "Autophosphorylation of the PDGF receptor in the kinase insert region regulates interactions with cell proteins" *Cell* 58:1121–1133.
Kazlauskas, Andrius et al. (1990) "Binding of GAP to activated PDGF receptors" *Science* 247:1578–1581.
Kirkness, Ewen F. et al. (1991) "Isolation, characterization, and localization of human genomic DNA encoding the β1 subunit of the GABA$_A$ receptor (GABRB1)" *Genomics* 10:985–995.
Koch, C. Anne et al. (1991) "SH2 and SH3 domains: Elements that control interactions of cytoplasmic signaling proteins" *Science* 252:668–674.
Koerner, T. J. et al. (1991) "High–expression vectors with multiple cloning sites for constructin of trpE fusion genes: pATH vectors" *Methods Enzymol.* 194:477–490.
Kozak, Marilyn (1989) "The scanning model for translation: An update" *J. Cell. Biol.* 108:229–241.
Kraus, M. H. et al. (1991) "Detection and isolation of novel protein–tyrosine kinase genes employing reduced stringency hybridization" *Methods Enzymol* 200:546–556.
Kypta, Robert M. et al. (1990) "Association between the PDGF receptor and members of the src family of tyrosine kinases" *Cell* 62:481–492.
Lee, James et al. (1989) "HER2 cytoplasmic domain generates normal mitogenic and transforming signals in a chimeric receptor" *EMBO J.* 8:167–173.

(List continued on next page.)

*Primary Examiner*—Robert A. Wax
*Assistant Examiner*—Eric Grimes
*Attorney, Agent, or Firm*—Knobbe, Martens, Olson & Bear

[57] ABSTRACT

A new substrate of epidermal growth factor receptor and certain other tyrosine kinase receptors denominated eps15 is disclosed, as well as, polynucleotides encoding eps15, antisense eps15 polynucleotide, triple helix eps15 polynucleotide, antibodies to eps15, and assays for determining eps15.

10 Claims, 1 Drawing Sheet

OTHER PUBLICATIONS

Lehvaslaiho, Keikki et al. (1989) "A chimeric EGF–R—neu proto–oncogene allows EGF to regulate neu tyrosine kinase and cell transformation" *EMBO J.* 8:159–166.

Lonardo, Fulvio et al. (1990) "The normal erbB–2 product is an atypical receptor–like tyrosine kinase with constitutive activity in the absence of ligand" *New Biol.* 2:992–1003.

Margolis, B. et al. (1989) "EGF induces tyrosine phosphorylation of phospholipase C–II: A potential mechanism for EGF receptor signalling" *Cell* 57:1101–1107.

McCombie, W. Richard et al. (1991) "The use of exonuclease III deletions in automated DNA sequencing" *Methods* 3:33–40.

McLachlan, Andrew D. et al. (1983) "Periodic features in the amino acid sequence of nematode myosin rod" *J. Mol. Bio.* 164:605–626.

Meisenhelder, Jill et al. (1989) "Phospholipase C–$\gamma$ is a substrate for the PDGF and EGF receptor protein–tyrosine kinases in vivo and in vitro" *Cell* 57:1109–1122.

Molloy, Christopher J. et al. (1989) "PDGF induction of tyrosine phosphorylation of GTPase activating protein" *Nature* 342:711–713.

Morrison, Deborah K. et al. (1989) "Direct activation of the serine/threonine kinase activity of Raf–1 through tyrosine phosphorylation by the PDGF $\beta$–receptor" *Cell* 58:649–657.

Morrison, Deborah K. et al. (1988) "Signal transduction from membrane to cytoplasm: Growth factors and membrane–bound oncogene products increase Raf–1 phosphorylation and associated protein kinase activity" *Proc. Natl. Acad. Sci. USA* 85:8855–8859.

Otsu, Masayuki et al. (1991) "Characterization of two 85 kd proteins that associate with receptor tyrosine kinases, middle–T/pp60$^{c-src}$ complexes, and PI3–kinase" *Cell* 65:91–104.

Rossi, John J. et al. (1991) "The potential use of catalytic RNAs in therapy of HIV infection and other diseases" *Pharmac. Ther.* 50:245–254.

Ruderman, Neil B. et al. (1990) "Activation of phosphatidylinositol 3–kinase by insulin" *Proc. Natl. Acad. Sci. USA* 87:1411–1415.

Segatto, Oreste et al. (1991) "The juxtamembrane regions of the epidermal growth factor receptor and gp185$^{erbB-2}$ determine the specificity of signal transduction" *Mol. Cell. Biol.* 11:3191–3202.

Skolnik, E. Y. et al. (1991) "Cloning of PI3 kinase—Associated p85 utilizing a novel method for expression/cloning of target proteins for receptor tyrosine kinases" *Cell* 65:83–90.

Ullrich, Axel et al. (1990) "Signal transduction by receptors with tyrosine kinase activity" *Cell* 61:203–212.

Varticovski, Lyuba et al. (1989) "The colony stimulating factor–1 receptor associates with and activates phosphatidylinositol–3 kinase" *Nature* 342:699–702.

Wahl, Matthew I. et al. (1989) "Platelet–derived growth factor induces rapid and sustained tyrosine phosphorylation of phospholipase C–$\gamma$ in quiescent BALB/c 3T3 Cells" *Mol. Cell. Biol.* 9:2934–2943.

Wolff, Jon A. et al. (1990) "Direct gene transfer into mouse muscle in vivo" *Science* 247:1465–1468.

SEQUENCE LISTING ( 1 ) GENERAL INFORMATION:

( i i i ) NUMBER OF SEQUENCES: 4

( 2 ) INFORMATION FOR SEQ ID NO:1:

( i ) SEQUENCE CHARACTERISTICS:
( A ) LENGTH: 4165 base pairs
( B ) TYPE: nucleic acid
( C ) STRANDEDNESS: double
( D ) TOPOLOGY: linear ( i i ) MOLECULE TYPE: cDNA ( i i i ) HYPOTHETICAL: NO ( i v ) ANTI-SENSE: NO ( i x ) FEATURE:
( A ) NAME/KEY: CDS
( B ) LOCATION: 21..2709

( x i ) SEQUENCE DESCRIPTION: SEQ ID NO:1:

| | | | | | | | | | | | | | | | | |
|---|---|---|---|---|---|---|---|---|---|---|---|---|---|---|---|---|
| AACCGCATGA | TGGAAACACC | ATG<br>Met<br>1 | GCT<br>Ala | GCG<br>Ala | GCG<br>Ala | GCC<br>Ala<br>5 | CAG<br>Gln | CTC<br>Leu | TCT<br>Ser | CTG<br>Leu | ACA<br>Thr<br>10 | | | | | 50 |
| CAG<br>Gln | TTA<br>Leu | TCA<br>Ser | AGT<br>Ser | GGG<br>Gly<br>15 | AAT<br>Asn | CCT<br>Pro | GTA<br>Val | TAT<br>Tyr | GAA<br>Glu<br>20 | AAA<br>Lys | TAC<br>Tyr | TAT<br>Tyr | AGA<br>Arg | CAG<br>Gln<br>25 | GTT<br>Val | 98 |
| GAT<br>Asp | ACA<br>Thr | GGC<br>Gly | AAT<br>Asn<br>30 | ACT<br>Thr | GGA<br>Gly | AGG<br>Arg | GTG<br>Val | TTG<br>Leu<br>35 | GCT<br>Ala | TCT<br>Ser | GAT<br>Asp | GCT<br>Ala | GCT<br>Ala<br>40 | GCT<br>Ala | TTC<br>Phe | 146 |
| CTG<br>Leu | AAA<br>Lys | AAA<br>Lys<br>45 | TCA<br>Ser | GGG<br>Gly | CTT<br>Leu | CCA<br>Pro | GAC<br>Asp<br>50 | TTG<br>Leu | ATA<br>Ile | CTT<br>Leu | GGA<br>Gly | AAG<br>Lys<br>55 | ATT<br>Ile | TGG<br>Trp | GAT<br>Asp | 194 |
| TTA<br>Leu | GCC<br>Ala<br>60 | GAC<br>Asp | ACA<br>Thr | GAT<br>Asp | GGC<br>Gly | AAA<br>Lys<br>65 | GGT<br>Gly | ATC<br>Ile | CTG<br>Leu | AAC<br>Asn | AAA<br>Lys<br>70 | CAA<br>Gln | GAA<br>Glu | TTC<br>Phe | TTT<br>Phe | 242 |
| GTT<br>Val<br>75 | GCT<br>Ala | TTG<br>Leu | CGT<br>Arg | CTT<br>Leu | GTG<br>Val<br>80 | GCA<br>Ala | TGT<br>Cys | GCC<br>Ala | CAG<br>Gln | AAT<br>Asn<br>85 | GGA<br>Gly | TTG<br>Leu | GAA<br>Glu | GTT<br>Val | TCA<br>Ser<br>90 | 290 |
| CTA<br>Leu | AGT<br>Ser | AGT<br>Ser | TTG<br>Leu | AAC<br>Asn<br>95 | CTG<br>Leu | GCT<br>Ala | GTT<br>Val | CCT<br>Pro | CCA<br>Pro<br>100 | CCA<br>Pro | AGA<br>Arg | TTT<br>Phe | CAT<br>His | GAT<br>Asp<br>105 | ACC<br>Thr | 338 |
| AGT<br>Ser | AGT<br>Ser | CCT<br>Pro | TTG<br>Leu<br>110 | CTA<br>Leu | ATC<br>Ile | AGT<br>Ser | GGA<br>Gly | ACC<br>Thr<br>115 | TCT<br>Ser | GCA<br>Ala | GCT<br>Ala | GAG<br>Glu | CTC<br>Leu<br>120 | CCA<br>Pro | TGG<br>Trp | 386 |
| GCT<br>Ala | GTA<br>Val | AAA<br>Lys<br>125 | CCT<br>Pro | GAA<br>Glu | GAT<br>Asp | AAG<br>Lys | GCC<br>Ala<br>130 | AAA<br>Lys | TAT<br>Tyr | GAT<br>Asp | GCA<br>Ala | ATA<br>Ile<br>135 | TTT<br>Phe | GAT<br>Asp | AGT<br>Ser | 434 |
| TTA<br>Leu | AGC<br>Ser<br>140 | CCA<br>Pro | GTG<br>Val | AAT<br>Asn | GGA<br>Gly | TTT<br>Phe<br>145 | CTG<br>Leu | TCT<br>Ser | GGT<br>Gly | GAT<br>Asp | AAA<br>Lys<br>150 | GTG<br>Val | AAA<br>Lys | CCA<br>Pro | GTG<br>Val | 482 |
| TTG<br>Leu<br>155 | CTC<br>Leu | AAC<br>Asn | TCT<br>Ser | AAG<br>Lys | TTA<br>Leu<br>160 | CCT<br>Pro | GTG<br>Val | GAT<br>Asp | ATC<br>Ile | CTT<br>Leu<br>165 | GGA<br>Gly | AGA<br>Arg | GTT<br>Val | TGG<br>Trp | GAG<br>Glu<br>170 | 530 |

```
TTG  AGT  GAT  ATT  GAC  CAT  GAT  GGA  ATG  CTT  GAC  AGA  GAT  GAG  TTT  GCA         578
Leu  Ser  Asp  Ile  Asp  His  Asp  Gly  Met  Leu  Asp  Arg  Asp  Glu  Phe  Ala
               175                      180                      185

GTT  GCC  ATG  TTT  TTG  GTA  TAC  TGT  GCA  CTG  GAG  AAA  GAA  CCT  GTG  CCA         626
Val  Ala  Met  Phe  Leu  Val  Tyr  Cys  Ala  Leu  Glu  Lys  Glu  Pro  Val  Pro
               190                      195                      200

ATG  TCC  TTG  CCT  CCA  GCC  TTG  GTG  CCA  CCA  TCT  AAG  AGA  AAA  ACG  TGG         674
Met  Ser  Leu  Pro  Pro  Ala  Leu  Val  Pro  Pro  Ser  Lys  Arg  Lys  Thr  Trp
          205                      210                      215

GTT  GTA  TCC  CCT  GCA  GAA  AAA  GCT  AAA  TAT  GAT  GAA  ATC  TTC  CTG  AAA         722
Val  Val  Ser  Pro  Ala  Glu  Lys  Ala  Lys  Tyr  Asp  Glu  Ile  Phe  Leu  Lys
     220                      225                      230

ACT  GAT  AAA  GAT  ATG  GAC  GGA  TTT  GTG  TCT  GGA  TTG  GAG  GTC  CGT  GAA         770
Thr  Asp  Lys  Asp  Met  Asp  Gly  Phe  Val  Ser  Gly  Leu  Glu  Val  Arg  Glu
235                      240                      245                      250

ATA  TTC  TTG  AAA  ACA  GGT  TTA  CCT  TCT  ACC  TTA  CTA  GCC  CAT  ATA  TGG         818
Ile  Phe  Leu  Lys  Thr  Gly  Leu  Pro  Ser  Thr  Leu  Leu  Ala  His  Ile  Trp
               255                      260                      265

TCA  TTA  TGC  GAC  ACA  AAG  GAC  TGT  GGG  AAG  CTT  TCA  AAG  GAT  CAG  TTT         866
Ser  Leu  Cys  Asp  Thr  Lys  Asp  Cys  Gly  Lys  Leu  Ser  Lys  Asp  Gln  Phe
               270                      275                      280

GCC  TTG  GCT  TTT  CAC  TTA  ATC  AGT  CAG  AAG  TTA  ATC  AAG  GGC  ATT  GAT         914
Ala  Leu  Ala  Phe  His  Leu  Ile  Ser  Gln  Lys  Leu  Ile  Lys  Gly  Ile  Asp
          285                      290                      295

CCT  CCT  CAC  GTT  CTT  ACT  CCT  GAA  ATG  ATT  CCA  CCA  TCA  GAC  AGG  GCC         962
Pro  Pro  His  Val  Leu  Thr  Pro  Glu  Met  Ile  Pro  Pro  Ser  Asp  Arg  Ala
     300                      305                      310

AGT  TTA  CAA  AAG  AAC  ATC  ATA  GGA  TCA  AGT  CCT  GTT  GCA  GAT  TTC  TCT        1010
Ser  Leu  Gln  Lys  Asn  Ile  Ile  Gly  Ser  Ser  Pro  Val  Ala  Asp  Phe  Ser
315                      320                      325                      330

GCT  ATT  AAG  GAA  CTA  GAT  ACT  CTT  AAC  AAT  GAA  ATA  GTT  GAC  CTA  CAG        1058
Ala  Ile  Lys  Glu  Leu  Asp  Thr  Leu  Asn  Asn  Glu  Ile  Val  Asp  Leu  Gln
               335                      340                      345

AGG  GAA  AAG  AAT  AAT  GTG  GAA  CAG  GAC  CTT  AAG  GAG  AAG  GAA  GAT  ACT        1106
Arg  Glu  Lys  Asn  Asn  Val  Glu  Gln  Asp  Leu  Lys  Glu  Lys  Glu  Asp  Thr
               350                      355                      360

ATT  AAA  CAG  AGG  ACA  AGT  GAG  GTT  CAG  GAT  CTT  CAA  GAT  GAA  GTT  CAA        1154
Ile  Lys  Gln  Arg  Thr  Ser  Glu  Val  Gln  Asp  Leu  Gln  Asp  Glu  Val  Gln
          365                      370                      375

AGG  GAG  AAT  ACT  AAT  CTG  CAA  AAA  CTA  CAG  GCC  CAG  AAA  CAG  CAG  GTA        1202
Arg  Glu  Asn  Thr  Asn  Leu  Gln  Lys  Leu  Gln  Ala  Gln  Lys  Gln  Gln  Val
     380                      385                      390

CAG  GAA  CTC  CTT  GAT  GAA  CTG  GAT  GAG  CAG  AAA  GCC  CAG  CTG  GAG  GAG        1250
Gln  Glu  Leu  Leu  Asp  Glu  Leu  Asp  Glu  Gln  Lys  Ala  Gln  Leu  Glu  Glu
395                      400                      405                      410

CAA  CTC  AAG  GAA  GTC  AGA  AAG  AAA  TGT  GCT  GAG  GAG  GCC  CAA  CTG  ATC        1298
Gln  Leu  Lys  Glu  Val  Arg  Lys  Lys  Cys  Ala  Glu  Glu  Ala  Gln  Leu  Ile
               415                      420                      425

TCT  TCT  CTG  AAA  GCT  GAA  TTA  ACT  AGT  CAG  GAA  TCG  CAG  ATC  TCC  ACT        1346
Ser  Ser  Leu  Lys  Ala  Glu  Leu  Thr  Ser  Gln  Glu  Ser  Gln  Ile  Ser  Thr
               430                      435                      440

TAT  GAA  GAA  GAA  TTG  GCA  AAA  GCT  AGA  GAA  GAG  CTG  AGC  CGT  CTA  CAG        1394
Tyr  Glu  Glu  Glu  Leu  Ala  Lys  Ala  Arg  Glu  Glu  Leu  Ser  Arg  Leu  Gln
          445                      450                      455

CAA  GAA  ACA  GCA  GAA  TTG  GAG  GAG  AGT  GTA  GAG  TCA  GGG  AAG  GCT  CAG        1442
Gln  Glu  Thr  Ala  Glu  Leu  Glu  Glu  Ser  Val  Glu  Ser  Gly  Lys  Ala  Gln
     460                      465                      470

TTG  GAA  CCT  CTT  CAG  CAG  CAC  CTA  CAA  GAT  TCA  CAA  CAG  GAA  ATT  AGT        1490
Leu  Glu  Pro  Leu  Gln  Gln  His  Leu  Gln  Asp  Ser  Gln  Gln  Glu  Ile  Ser
475                      480                      485                      490
```

| | | | | | | | | | | | | | | | | |
|---|---|---|---|---|---|---|---|---|---|---|---|---|---|---|---|---|
| TCA | ATG | CAA | ATG | AAA | CTG | ATG | GAA | ATG | AAA | GAT | TTG | GAA | AAT | CAT | AAT | 1538 |
| Ser | Met | Gln | Met | Lys 495 | Leu | Met | Glu | Met | Lys 500 | Asp | Leu | Glu | Asn | His 505 | Asn | |
| AGT | CAG | TTA | AAT | TGG | TGC | AGT | AGC | CCA | CAC | AGC | ATT | CTT | GTA | AAC | GGA | 1586 |
| Ser | Gln | Leu | Asn 510 | Trp | Cys | Ser | Ser | Pro 515 | His | Ser | Ile | Leu | Val 520 | Asn | Gly | |
| GCT | ACA | GAT | TAT | TGC | AGC | CTC | AGC | ACC | AGC | AGC | AGT | GAA | ACA | GCC | AAC | 1634 |
| Ala | Thr | Asp 525 | Tyr | Cys | Ser | Leu | Ser 530 | Thr | Ser | Ser | Ser | Glu 535 | Thr | Ala | Asn | |
| CTT | AAT | GAA | CAT | GTT | GAA | GGC | CAG | AGC | AAC | CTA | GAG | TCT | GAG | CCC | ATA | 1682 |
| Leu | Asn 540 | Glu | His | Val | Glu | Gly 545 | Gln | Ser | Asn | Leu | Glu 550 | Ser | Glu | Pro | Ile | |
| CAC | CAG | GAA | TCT | CCA | GCA | AGA | AGT | AGT | CCT | GAA | CTA | CTG | CCT | TCT | GGT | 1730 |
| His 555 | Gln | Glu | Ser | Pro | Ala 560 | Arg | Ser | Ser | Pro | Glu 565 | Leu | Leu | Pro | Ser | Gly 570 | |
| GTG | ACT | GAT | GAA | AAT | GAG | GTG | ACT | ACA | GCT | GTT | ACT | GAA | AAA | GTT | TGT | 1778 |
| Val | Thr | Asp | Glu | Asn 575 | Glu | Val | Thr | Thr | Ala 580 | Val | Thr | Glu | Lys | Val 585 | Cys | |
| TCT | GAA | CTC | GAC | AAT | AAT | AGA | CAT | TCA | AAA | GAG | GAA | GAT | CCA | TTT | AAT | 1826 |
| Ser | Glu | Leu | Asp 590 | Asn | Asn | Arg | His | Ser 595 | Lys | Glu | Glu | Asp | Pro 600 | Phe | Asn | |
| GTA | GAC | TCA | AGT | TCG | CTG | ACA | GGT | CCA | GTT | GCA | GAT | ACA | AAC | TTG | GAT | 1874 |
| Val | Asp | Ser 605 | Ser | Ser | Leu | Thr | Gly 610 | Pro | Val | Ala | Asp | Thr 615 | Asn | Leu | Asp | |
| TTT | TTC | CAG | TCT | GAT | CCT | TTT | GTT | GGC | AGT | GAT | CCT | TTC | AAG | GAT | GAT | 1922 |
| Phe | Phe | Gln 620 | Ser | Asp | Pro | Phe | Val 625 | Gly | Ser | Asp | Pro | Phe 630 | Lys | Asp | Asp | |
| CCT | TTT | GGA | AAA | ATC | GAT | CCA | TTT | GGT | GGT | GAT | CCT | TTC | AAA | GGT | TCA | 1970 |
| Pro 635 | Phe | Gly | Lys | Ile | Asp 640 | Pro | Phe | Gly | Gly | Asp 645 | Pro | Phe | Lys | Gly | Ser 650 | |
| GAT | CCA | TTT | GCA | TCA | GAC | TGT | TTC | TTC | AGG | CAA | TCT | ACT | GAT | CCT | TTT | 2018 |
| Asp | Pro | Phe | Ala | Ser 655 | Asp | Cys | Phe | Phe | Arg 660 | Gln | Ser | Thr | Asp | Pro 665 | Phe | |
| GCC | ACT | TCA | AGC | ACT | GAC | CCT | TTC | AGT | GCA | GCC | AAC | AAT | AGC | AGT | ATT | 2066 |
| Ala | Thr | Ser | Ser 670 | Thr | Asp | Pro | Phe | Ser 675 | Ala | Ala | Asn | Asn | Ser 680 | Ser | Ile | |
| ACA | TCG | GTA | GAA | ACG | TTG | AAG | CAC | AAT | GAT | CCT | TTT | GCT | CCT | GGT | GGA | 2114 |
| Thr | Ser | Val 685 | Glu | Thr | Leu | Lys | His 690 | Asn | Asp | Pro | Phe | Ala 695 | Pro | Gly | Gly | |
| ACA | GTT | GTT | GCA | GCA | AGC | GAT | TCA | GCC | ACA | GAC | CCC | TTT | GCT | TCT | GTT | 2162 |
| Thr | Val 700 | Val | Ala | Ala | Ser | Asp 705 | Ser | Ala | Thr | Asp | Pro 710 | Phe | Ala | Ser | Val | |
| TTT | GGG | AAT | GAA | TCA | TTT | GGA | GGT | GGA | TTT | GCT | GAC | TTC | AGC | ACA | TTG | 2210 |
| Phe 715 | Gly | Asn | Glu | Ser | Phe 720 | Gly | Gly | Gly | Phe | Ala 725 | Asp | Phe | Ser | Thr | Leu 730 | |
| TCA | AAG | GTC | AAC | AAT | GAA | GAT | CCT | TTT | CGT | TCA | GCC | ACA | TCG | AGC | TCT | 2258 |
| Ser | Lys | Val | Asn | Asn 735 | Glu | Asp | Pro | Phe | Arg 740 | Ser | Ala | Thr | Ser | Ser 745 | Ser | |
| GTC | AGC | AAC | GTA | GTG | ATT | ACA | AAA | AAT | GTA | TTT | GAG | GAA | ACA | TCG | GTC | 2306 |
| Val | Ser | Asn | Val 750 | Val | Ile | Thr | Lys | Asn 755 | Val | Phe | Glu | Glu | Thr 760 | Ser | Val | |
| AAA | AGT | GAA | GAT | GAA | CCC | CCA | GCA | CTG | CCA | CCA | AAG | ATC | GGA | ACT | CCA | 2354 |
| Lys | Ser | Glu | Asp 765 | Glu | Pro | Pro | Ala | Leu 770 | Pro | Pro | Lys | Ile | Gly 775 | Thr | Pro | |
| ACA | AGA | CCC | TGC | CCT | CTA | CCA | CCT | GGG | AAA | AGA | TCC | ATC | AAC | AAA | TTG | 2402 |
| Thr | Arg 780 | Pro | Cys | Pro | Leu | Pro 785 | Pro | Gly | Lys | Arg | Ser 790 | Ile | Asn | Lys | Leu | |
| GAT | TCT | CCT | GAT | CCC | TTT | AAA | CTG | AAT | GAT | CCA | TTT | CAG | CCT | TTC | CCA | 2450 |
| Asp | Ser | Pro | Asp 795 | Pro | Phe | Lys | Leu | Asn 800 | Asp | Pro | Phe | Gln | Pro 805 | Phe | Pro | |

| | | | | | | | | | | | | | | | | |
|---|---|---|---|---|---|---|---|---|---|---|---|---|---|---|---|---|
| GGC | AAC | GAT | AGC | CCC | AAA | GAA | AAA | GAT | CCT | GAA | ATG | TTT | TGT | GAT | CCA | 2498 |
| Gly | Asn | Asp | Ser | Pro | Lys | Glu | Lys | Asp | Pro | Glu | Met | Phe | Cys | Asp | Pro | |
| | | | | 815 | | | | 820 | | | | | | 825 | | |
| TTC | ACT | TCT | GCT | ACT | ACC | ACT | ACC | AAT | AAA | GAG | GCT | GAT | CCA | AGC | AAT | 2546 |
| Phe | Thr | Ser | Ala | Thr | Thr | Thr | Thr | Asn | Lys | Glu | Ala | Asp | Pro | Ser | Asn | |
| | | | 830 | | | | | 835 | | | | | 840 | | | |
| TTT | GCC | AAC | TTC | AGT | GCT | TAT | CCC | TCT | GAA | GAA | GAT | ATG | ATC | GAA | TGG | 2594 |
| Phe | Ala | Asn | Phe | Ser | Ala | Tyr | Pro | Ser | Glu | Glu | Asp | Met | Ile | Glu | Trp | |
| | | 845 | | | | | 850 | | | | | 855 | | | | |
| GCC | AAG | AGG | GAA | AGT | GAG | AGA | GAG | GAA | GAG | CAG | AGG | CTT | GCC | CGA | CTA | 2642 |
| Ala | Lys | Arg | Glu | Ser | Glu | Arg | Glu | Glu | Glu | Gln | Arg | Leu | Ala | Arg | Leu | |
| | 860 | | | | | 865 | | | | | 870 | | | | | |
| AAT | CAG | CAG | GAA | CAA | GAA | GAC | TTA | GAA | CTG | GCT | ATT | GCA | CTC | AGC | AAA | 2690 |
| Asn | Gln | Gln | Glu | Gln | Glu | Asp | Leu | Glu | Leu | Ala | Ile | Ala | Leu | Ser | Lys | |
| 875 | | | | | 880 | | | | | 885 | | | | | 890 | |
| TCT | GAG | ATA | TCA | GAA | GCA | T | GAAGAATTCT | CTTGTTCTTT | GGCAACAATA | | | | | | | 2739 |
| Ser | Glu | Ile | Ser | Glu | Ala | | | | | | | | | | | |
| | | | | 895 | | | | | | | | | | | | |

| | | | | |
|---|---|---|---|---|
| TAGTATTCTT | CTTCCTGAAT | ACTGAAACTA | TTTACAATGT | GTATCAAAAC | TACCTGTGAG | 2799 |
| CATGGGAATA | CAAAAGGTTT | GAGATTCCTG | TAAATGTGAC | AAAATTTTAG | GATTTTTTTT | 2859 |
| TTTTCTTCAT | TACAGATTCG | TCTTTTTTTT | TTTTCTTAT | AAAAGCCGTA | ACCCAGTCAG | 2919 |
| ACAAATTCAC | CTTCACTTAG | GCCCTGTTC | TGGTATACAT | TTACTGTGAG | CTTTGCCTG | 2979 |
| CCTGTGCTAT | TTTACTTGTA | AAGCTAGAGC | ACCCAAGCTT | CTGCCTTCTG | GAATATAGAG | 3039 |
| AAATAGTTTC | ACCCTGCACT | ACCCTGTTCT | GTAGTTATTC | TGATGATAGC | CAGTGAGGTT | 3099 |
| CTTAAAGTTT | GCAGTATTCT | CCCCTGATTG | GAATGGTTGA | GTGAGGGTAA | GGGAAAGAAT | 3159 |
| ATCTTATTTC | TTTTATGATT | GGTGCAAATT | GGCTAAAGTG | CATTTTAAA | TTTCCTCTAC | 3219 |
| TTAATTTGTT | TTTCAGAGAT | AAGGAAAAAT | ATTTTGCACA | GATTTACTCC | ACTATGGAAA | 3279 |
| AGGGATGCTG | TAGGTTGAAC | CATTATAGCC | TCAGATTCGA | TCTTTTCCTA | ACTAAAAATA | 3339 |
| TTAAAGCCTC | ATGTGTGAAA | TAAATTTTA | AAAAGATTTA | TCTGGATTTA | GAGAATTTTA | 3399 |
| GATCAACAGA | TACCTCTCAG | TGTGTTTGCT | AATTAATAAA | AATCAGTTTC | TTACAAATAA | 3459 |
| AGTTTGTAAG | AAAATGTTCA | TTTTAAGTGA | TAGATAGTGG | AGAAAATTTA | TCACCTAAAA | 3519 |
| TATACCCATC | AGTATAAGGC | AAGCAAAAGT | CTTAACATGG | CAGCCATTCT | GCCTTTGCCG | 3579 |
| TGGCCCTGTC | CTGTTTAGTT | CTTAGTGGGT | TAATTTTGT | ACTTTTGCAG | AAGAAACTTC | 3639 |
| AGCAAGCTAG | AACTGGAAGG | TACTTTAATT | TTTCATATAT | ATTTGTTTTT | TTTTTTTTAA | 3699 |
| TGAAGGCTCA | TTTACTTGAA | ATGTAAAAAC | TTTCACTGAA | TACAAATAGA | AAAAGTGATG | 3759 |
| TGTTTTATAT | CATATTGCTT | TTTGTCCATC | TTTGTGGTTT | AGTTATTTA | CTCACTTCAT | 3819 |
| GTTTTTCACC | TATAAAATTG | TCAAGCTAGC | AAAAAAACTC | TTGTTTTTT | AATTGGGAGA | 3879 |
| GAAGAGACCT | GCCAGATTAT | CAGACCTCTT | CATGTTAAAA | GACCATCTCC | TGTAAAACTG | 3939 |
| ACCTAGTGGA | CAAGCTGAAT | TTGAAATAGA | CTGTGAAGTA | AGCTGTAACT | TGTCATTTTA | 3999 |
| ATTTTGTTTA | ACACGGTTAC | TGACTTAGAT | GATGTATTAA | ATACCAAGAT | AAAGAAAAAT | 4059 |
| GCACCTAAAA | TCTAATTAGA | ATTCTCTGGG | TCACCAAGTC | AAGGTGGTAT | TGATCTGTGT | 4119 |
| TAATCTGAGT | AACTTATTGC | CTAGCCTATA | AATAAATTCC | AATATC | | 4165 |

( 2 ) INFORMATION FOR SEQ ID NO:2:

( i ) SEQUENCE CHARACTERISTICS:
        ( A ) LENGTH: 896 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

| Met | Ala | Ala | Ala | Ala | Gln | Leu | Ser | Leu | Thr | Gln | Leu | Ser | Ser | Gly | Asn |
| 1 | | | | 5 | | | | | 10 | | | | | 15 | |

| Pro | Val | Tyr | Glu | Lys | Tyr | Tyr | Arg | Gln | Val | Asp | Thr | Gly | Asn | Thr | Gly |
| | | | 20 | | | | | 25 | | | | 30 | | | |

| Arg | Val | Leu | Ala | Ser | Asp | Ala | Ala | Phe | Leu | Lys | Lys | Ser | Gly | Leu |
| | | 35 | | | | 40 | | | | | 45 | | | |

| Pro | Asp | Leu | Ile | Leu | Gly | Lys | Ile | Trp | Asp | Leu | Ala | Asp | Thr | Asp | Gly |
| | 50 | | | | | 55 | | | | | 60 | | | | |

| Lys | Gly | Ile | Leu | Asn | Lys | Gln | Glu | Phe | Phe | Val | Ala | Leu | Arg | Leu | Val |
| 65 | | | | | 70 | | | | 75 | | | | | | 80 |

| Ala | Cys | Ala | Gln | Asn | Gly | Leu | Glu | Val | Ser | Leu | Ser | Ser | Leu | Asn | Leu |
| | | | | 85 | | | | | 90 | | | | | 95 | |

| Ala | Val | Pro | Pro | Pro | Arg | Phe | His | Asp | Thr | Ser | Ser | Pro | Leu | Leu | Ile |
| | | | 100 | | | | | 105 | | | | | 110 | | |

| Ser | Gly | Thr | Ser | Ala | Ala | Glu | Leu | Pro | Trp | Ala | Val | Lys | Pro | Glu | Asp |
| | | 115 | | | | | 120 | | | | | 125 | | | |

| Lys | Ala | Lys | Tyr | Asp | Ala | Ile | Phe | Asp | Ser | Leu | Ser | Pro | Val | Asn | Gly |
| | 130 | | | | | 135 | | | | | 140 | | | | |

| Phe | Leu | Ser | Gly | Asp | Lys | Val | Lys | Pro | Val | Leu | Asn | Ser | Lys | Leu |
| 145 | | | | | 150 | | | | | 155 | | | | | 160 |

| Pro | Val | Asp | Ile | Leu | Gly | Arg | Val | Trp | Glu | Leu | Ser | Asp | Ile | Asp | His |
| | | | | 165 | | | | | 170 | | | | | 175 | |

| Asp | Gly | Met | Leu | Asp | Arg | Asp | Glu | Phe | Ala | Val | Ala | Met | Phe | Leu | Val |
| | | | 180 | | | | | 185 | | | | | 190 | | |

| Tyr | Cys | Ala | Leu | Glu | Lys | Glu | Pro | Val | Pro | Met | Ser | Leu | Pro | Pro | Ala |
| | | 195 | | | | | 200 | | | | | 205 | | | |

| Leu | Val | Pro | Pro | Ser | Lys | Arg | Lys | Thr | Trp | Val | Val | Ser | Pro | Ala | Glu |
| | 210 | | | | | 215 | | | | | 220 | | | | |

| Lys | Ala | Lys | Tyr | Asp | Glu | Ile | Phe | Leu | Lys | Thr | Asp | Lys | Asp | Met | Asp |
| 225 | | | | | 230 | | | | | 235 | | | | | 240 |

| Gly | Phe | Val | Ser | Gly | Leu | Glu | Val | Arg | Glu | Ile | Phe | Leu | Lys | Thr | Gly |
| | | | | 245 | | | | | 250 | | | | | 255 | |

| Leu | Pro | Ser | Thr | Leu | Leu | Ala | His | Ile | Trp | Ser | Leu | Cys | Asp | Thr | Lys |
| | | | 260 | | | | | 265 | | | | | 270 | | |

| Asp | Cys | Gly | Lys | Leu | Ser | Lys | Asp | Gln | Phe | Ala | Leu | Ala | Phe | His | Leu |
| | | 275 | | | | | 280 | | | | | 285 | | | |

| Ile | Ser | Gln | Lys | Leu | Ile | Lys | Gly | Ile | Asp | Pro | Pro | His | Val | Leu | Thr |
| | 290 | | | | | 295 | | | | | 300 | | | | |

| Pro | Glu | Met | Ile | Pro | Pro | Ser | Asp | Arg | Ala | Ser | Leu | Gln | Lys | Asn | Ile |
| 305 | | | | | 310 | | | | | 315 | | | | | 320 |

| Ile | Gly | Ser | Ser | Pro | Val | Ala | Asp | Phe | Ser | Ala | Ile | Lys | Glu | Leu | Asp |
| | | | | 325 | | | | | 330 | | | | | 335 | |

| Thr | Leu | Asn | Asn | Glu | Ile | Val | Asp | Leu | Gln | Arg | Glu | Lys | Asn | Asn | Val |
| | | | 340 | | | | | 345 | | | | | 350 | | |

| Glu | Gln | Asp | Leu | Lys | Glu | Lys | Glu | Asp | Thr | Ile | Lys | Gln | Arg | Thr | Ser |
| | | 355 | | | | | 360 | | | | | 365 | | | |

| Glu | Val | Gln | Asp | Leu | Gln | Asp | Glu | Val | Gln | Arg | Glu | Asn | Thr | Asn | Leu |
| | 370 | | | | | 375 | | | | | 380 | | | | |

| Gln | Lys | Leu | Gln | Ala | Gln | Lys | Gln | Gln | Val | Gln | Glu | Leu | Leu | Asp | Glu |
| 385 | | | | | 390 | | | | | 395 | | | | | 400 |

| Leu | Asp | Glu | Gln | Lys | Ala | Gln | Leu | Glu | Glu | Gln | Leu | Lys | Glu | Val | Arg |

|     |     |     |     |     |     |     | 405 |     |     |     |     | 410 |     |     |     |     | 415 |     |     |
|-----|-----|-----|-----|-----|-----|-----|-----|-----|-----|-----|-----|-----|-----|-----|-----|-----|-----|-----|-----|

Lys Lys Cys Ala Glu Glu Ala Gln Leu Ile Ser Ser Leu Lys Ala Glu
            420             425             430

Leu Thr Ser Gln Glu Ser Gln Ile Ser Thr Tyr Glu Glu Glu Leu Ala
            435             440             445

Lys Ala Arg Glu Glu Leu Ser Arg Leu Gln Gln Glu Thr Ala Glu Leu
        450             455             460

Glu Glu Ser Val Glu Ser Gly Lys Ala Gln Leu Glu Pro Leu Gln Gln
465             470             475                         480

His Leu Gln Asp Ser Gln Gln Glu Ile Ser Ser Met Gln Met Lys Leu
            485             490             495

Met Glu Met Lys Asp Leu Glu Asn His Asn Ser Gln Leu Asn Trp Cys
            500             505             510

Ser Ser Pro His Ser Ile Leu Val Asn Gly Ala Thr Asp Tyr Cys Ser
            515             520             525

Leu Ser Thr Ser Ser Ser Glu Thr Ala Asn Leu Asn Glu His Val Glu
        530             535             540

Gly Gln Ser Asn Leu Glu Ser Glu Pro Ile His Gln Glu Ser Pro Ala
545             550             555                         560

Arg Ser Ser Pro Glu Leu Leu Pro Ser Gly Val Thr Asp Glu Asn Glu
            565             570             575

Val Thr Thr Ala Val Thr Glu Lys Val Cys Ser Glu Leu Asp Asn Asn
            580             585             590

Arg His Ser Lys Glu Glu Asp Pro Phe Asn Val Asp Ser Ser Ser Leu
            595             600             605

Thr Gly Pro Val Ala Asp Thr Asn Leu Asp Phe Phe Gln Ser Asp Pro
    610             615             620

Phe Val Gly Ser Asp Pro Phe Lys Asp Asp Pro Phe Gly Lys Ile Asp
625             630             635                         640

Pro Phe Gly Gly Asp Pro Phe Lys Gly Ser Asp Pro Phe Ala Ser Asp
            645             650             655

Cys Phe Phe Arg Gln Ser Thr Asp Pro Phe Ala Thr Ser Ser Thr Asp
        660             665             670

Pro Phe Ser Ala Ala Asn Asn Ser Ser Ile Thr Ser Val Glu Thr Leu
        675             680             685

Lys His Asn Asp Pro Phe Ala Pro Gly Gly Thr Val Val Ala Ala Ser
    690             695             700

Asp Ser Ala Thr Asp Pro Phe Ala Ser Val Phe Gly Asn Glu Ser Phe
705             710             715                         720

Gly Gly Gly Phe Ala Asp Phe Ser Thr Leu Ser Lys Val Asn Asn Glu
            725             730             735

Asp Pro Phe Arg Ser Ala Thr Ser Ser Val Ser Asn Val Val Ile
        740             745             750

Thr Lys Asn Val Phe Glu Glu Thr Ser Val Lys Ser Glu Asp Glu Pro
    755             760             765

Pro Ala Leu Pro Pro Lys Ile Gly Thr Pro Thr Arg Pro Cys Pro Leu
    770             775             780

Pro Pro Gly Lys Arg Ser Ile Asn Lys Leu Asp Ser Pro Asp Pro Phe
785             790             795                         800

Lys Leu Asn Asp Pro Phe Gln Pro Phe Pro Gly Asn Asp Ser Pro Lys
            805             810             815

Glu Lys Asp Pro Glu Met Phe Cys Asp Pro Phe Thr Ser Ala Thr Thr
            820             825             830

|     |     |     |     |     |     |     |     |     |     |     |     |     |     |     |     |
|-----|-----|-----|-----|-----|-----|-----|-----|-----|-----|-----|-----|-----|-----|-----|-----|
| Thr | Thr | Asn | Lys | Glu | Ala | Asp | Pro | Ser | Asn | Phe | Ala | Asn | Phe | Ser | Ala |
|     |     | 835 |     |     |     |     | 840 |     |     |     |     | 845 |     |     |     |
| Tyr | Pro | Ser | Glu | Glu | Asp | Met | Ile | Glu | Trp | Ala | Lys | Arg | Glu | Ser | Glu |
|     | 850 |     |     |     |     | 855 |     |     |     |     | 860 |     |     |     |     |
| Arg | Glu | Glu | Glu | Gln | Arg | Leu | Ala | Arg | Leu | Asn | Gln | Gln | Glu | Gln | Glu |
| 865 |     |     |     | 870 |     |     |     |     |     | 875 |     |     |     |     | 880 |
| Asp | Leu | Glu | Leu | Ala | Ile | Ala | Leu | Ser | Lys | Ser | Glu | Ile | Ser | Glu | Ala |
|     |     |     |     | 885 |     |     |     |     | 890 |     |     |     |     | 895 |     |

( 2 ) INFORMATION FOR SEQ ID NO:3:

( i ) SEQUENCE CHARACTERISTICS:
        ( A ) LENGTH: 3033 base pairs
        ( B ) TYPE: nucleic acid
        ( C ) STRANDEDNESS: double
        ( D ) TOPOLOGY: linear ( i i ) MOLECULE TYPE: cDNA ( i i i ) HYPOTHETICAL: NO ( i v ) ANTI-SENSE: NO ( i x ) FEATURE:
        ( A ) NAME/KEY: CDS
        ( B ) LOCATION: 111..2802

( x i ) SEQUENCE DESCRIPTION: SEQ ID NO:3:

| | | | | | | |
|---|---|---|---|---|---|---|
| CCGAGACGCC | CGGCGCCGGC | CTCGCCTACG | GCCTGTCCCT | CCGCCTCCTT | CCCGCCCCGG | 60 |

| | | | | | | |
|---|---|---|---|---|---|---|
| GCCCCCGTCC | GTCCGTCCTT | CCTTCCCCTC | CCGTGCATGA | TGGAAACACC | ATG GCT | 116 |
| | | | | | Met Ala | |
| | | | | | 1 | |

| | | | | | | | | | | | | | | | |
|---|---|---|---|---|---|---|---|---|---|---|---|---|---|---|---|
| GCG | GCA | GCC | CAG | CTC | TCC | CTG | ACA | CAG | TTG | TCA | AGT | GGG | AAT | CCT GTA | 164 |
| Ala | Ala | Ala | Gln | Leu | Ser | Leu | Thr | Gln | Leu | Ser | Ser | Gly | Asn | Pro Val | |
| | | 5 | | | | | 10 | | | | | 15 | | | |

| | | | | | | | | | | | | | | | |
|---|---|---|---|---|---|---|---|---|---|---|---|---|---|---|---|
| TAT | GAA | AAA | TAC | TAC | AGA | CAG | GTT | GAG | GCA | GGC | AAT | ACT | GGA | AGG GTG | 212 |
| Tyr | Glu | Lys | Tyr | Tyr | Arg | Gln | Val | Glu | Ala | Gly | Asn | Thr | Gly | Arg Val | |
| | 20 | | | | | 25 | | | | | 30 | | | | |

| | | | | | | | | | | | | | | | |
|---|---|---|---|---|---|---|---|---|---|---|---|---|---|---|---|
| TTG | GCG | TTA | GAT | GCT | GCT | GCA | TTC | CTG | AAA | AAG | TCA | GGG | CTT | CCA GAC | 260 |
| Leu | Ala | Leu | Asp | Ala | Ala | Ala | Phe | Leu | Lys | Lys | Ser | Gly | Leu | Pro Asp | |
| 35 | | | | | 40 | | | | | 45 | | | | | 50 |

| | | | | | | | | | | | | | | | |
|---|---|---|---|---|---|---|---|---|---|---|---|---|---|---|---|
| TTG | ATT | CTT | GGA | AAG | ATT | TGG | GAT | TTA | GCT | GAC | ACA | GAT | GGC | AAA GGT | 308 |
| Leu | Ile | Leu | Gly | Lys | Ile | Trp | Asp | Leu | Ala | Asp | Thr | Asp | Gly | Lys Gly | |
| | | | | 55 | | | | | 60 | | | | | 65 | |

| | | | | | | | | | | | | | | | |
|---|---|---|---|---|---|---|---|---|---|---|---|---|---|---|---|
| GTC | CTG | AGC | AAA | CAA | GAA | TTC | TTT | GTT | GCT | TTA | CGG | CTT | GTG | GCA TGT | 356 |
| Val | Leu | Ser | Lys | Gln | Glu | Phe | Phe | Val | Ala | Leu | Arg | Leu | Val | Ala Cys | |
| | | | 70 | | | | | 75 | | | | | 80 | | |

| | | | | | | | | | | | | | | | |
|---|---|---|---|---|---|---|---|---|---|---|---|---|---|---|---|
| GCT | CAG | AAT | GGA | CTG | GAA | GTT | TCA | CTG | AGT | AGC | CTA | AGT | CTG | GCT GTT | 404 |
| Ala | Gln | Asn | Gly | Leu | Glu | Val | Ser | Leu | Ser | Ser | Leu | Ser | Leu | Ala Val | |
| | | 85 | | | | | 90 | | | | | 95 | | | |

| | | | | | | | | | | | | | | | |
|---|---|---|---|---|---|---|---|---|---|---|---|---|---|---|---|
| CCT | CCA | CCA | AGA | TTT | CAT | GAC | TCC | AGC | AGT | CCG | TTG | CTA | ACC | AGT GGG | 452 |
| Pro | Pro | Pro | Arg | Phe | His | Asp | Ser | Ser | Ser | Pro | Leu | Leu | Thr | Ser Gly | |
| | | 100 | | | | | 105 | | | | | 110 | | | |

| | | | | | | | | | | | | | | | |
|---|---|---|---|---|---|---|---|---|---|---|---|---|---|---|---|
| CCC | TCA | GTT | GCT | GAG | CTC | CCG | TGG | GCT | GTA | AAG | TCT | GAA | GAT | AAA GCC | 500 |
| Pro | Ser | Val | Ala | Glu | Leu | Pro | Trp | Ala | Val | Lys | Ser | Glu | Asp | Lys Ala | |
| 115 | | | | | 120 | | | | | 125 | | | | | 130 |

| | | | | | | | | | | | | | | | |
|---|---|---|---|---|---|---|---|---|---|---|---|---|---|---|---|
| AAA | TAT | GAT | GCA | ATT | TTT | GAC | AGT | TTA | AGC | CCA | GTG | GAT | GGA | TTT TTG | 548 |
| Lys | Tyr | Asp | Ala | Ile | Phe | Asp | Ser | Leu | Ser | Pro | Val | Asp | Gly | Phe Leu | |
| | | | | 135 | | | | | 140 | | | | | 145 | |

| | | | | | | | | | | | | | | | |
|---|---|---|---|---|---|---|---|---|---|---|---|---|---|---|---|
| TCT | GGT | GAT | AAA | GTG | AAA | CCA | GTG | TTG | CTC | AAC | TCT | AAG | TTA | CCT GTG | 596 |
| Ser | Gly | Asp | Lys | Val | Lys | Pro | Val | Leu | Leu | Asn | Ser | Lys | Leu | Pro Val | |
| | | | 150 | | | | | 155 | | | | | 160 | | |

| | | | | | | | | | | | | | | | |
|---|---|---|---|---|---|---|---|---|---|---|---|---|---|---|---|
| GAA | ATC | CTT | GGA | AGA | GTT | TGG | GAG | TTG | AGT | GAT | ATT | GAC | CAC | GAT GGA | 644 |

```
Glu  Ile  Leu  Gly  Arg  Val  Trp  Glu  Leu  Ser  Asp  Ile  Asp  His  Asp  Gly
          165                     170                     175

AAG  CTG  GAC  AGA  GAT  GAG  TTT  GCA  GTT  GCC  ATG  TTT  TTG  GTA  TAC  TGT      692
Lys  Leu  Asp  Arg  Asp  Glu  Phe  Ala  Val  Ala  Met  Phe  Leu  Val  Tyr  Cys
     180                     185                     190

GCA  CTG  GAG  AAA  GAA  CCT  GTG  CCA  ATG  TCC  TTG  CCT  CCA  GCC  TTG  GTG      740
Ala  Leu  Glu  Lys  Glu  Pro  Val  Pro  Met  Ser  Leu  Pro  Pro  Ala  Leu  Val
195                     200                     205                     210

CCA  CCT  TCT  AAG  AGA  AAA  ACG  TGG  GTT  GTA  TCC  CCT  GCA  GAA  AAA  GCT      788
Pro  Pro  Ser  Lys  Arg  Lys  Thr  Trp  Val  Val  Ser  Pro  Ala  Glu  Lys  Ala
                    215                     220                     225

AAA  TAT  GAT  GAA  ATT  TTT  CTG  AAA  ACT  GAT  AAG  GAT  ATG  GAT  GGA  TAT      836
Lys  Tyr  Asp  Glu  Ile  Phe  Leu  Lys  Thr  Asp  Lys  Asp  Met  Asp  Gly  Tyr
               230                     235                     240

GTG  TCT  GGA  CTG  GAG  GTC  CGT  GAA  ACC  TTC  CTG  AAA  ACA  GGT  TTA  CCT      884
Val  Ser  Gly  Leu  Glu  Val  Arg  Glu  Thr  Phe  Leu  Lys  Thr  Gly  Leu  Pro
          245                     250                     255

TCT  GCC  TTG  CTA  GCC  CAC  ATT  TGG  TCA  CTA  TGT  GAC  ACA  AAG  GGC  TGT      932
Ser  Ala  Leu  Leu  Ala  His  Ile  Trp  Ser  Leu  Cys  Asp  Thr  Lys  Gly  Cys
260                     265                     270

GGG  AAG  CTT  TCA  AAA  GAC  CAG  TTT  GCC  TTG  GCT  TTT  CAC  TTA  ATC  AAT      980
Gly  Lys  Leu  Ser  Lys  Asp  Gln  Phe  Ala  Leu  Ala  Phe  His  Leu  Ile  Asn
275                     280                     285                     290

CAG  AAG  TTA  ATA  AAA  GGC  ATT  GAC  CCT  CCT  CAT  AGT  CTC  ACT  CCT  GAG     1028
Gln  Lys  Leu  Ile  Lys  Gly  Ile  Asp  Pro  Pro  His  Ser  Leu  Thr  Pro  Glu
                    295                     300                     305

ATG  ATT  CCA  CCA  TCA  GAC  AGA  TCC  AGT  TTA  CAA  AAG  AAC  ATC  ACA  GGA     1076
Met  Ile  Pro  Pro  Ser  Asp  Arg  Ser  Ser  Leu  Gln  Lys  Asn  Ile  Thr  Gly
               310                     315                     320

TCA  AGT  CCT  GTT  GCA  GAT  TTT  TCT  GCT  ATT  AAG  GAA  CTA  GAT  ACC  CTT     1124
Ser  Ser  Pro  Val  Ala  Asp  Phe  Ser  Ala  Ile  Lys  Glu  Leu  Asp  Thr  Leu
          325                     330                     335

AAC  AAT  GAA  ATA  GTT  GAC  CTG  CAG  AGG  GAA  AAG  AAC  AAT  GTG  GAG  CAG     1172
Asn  Asn  Glu  Ile  Val  Asp  Leu  Gln  Arg  Glu  Lys  Asn  Asn  Val  Glu  Gln
340                     345                     350

GAC  CTT  AAA  GAG  AAG  GAA  GAC  ACA  GTT  AAG  CAG  AGG  ACC  AGT  GAG  GTT     1220
Asp  Leu  Lys  Glu  Lys  Glu  Asp  Thr  Val  Lys  Gln  Arg  Thr  Ser  Glu  Val
355                     360                     365                     370

CAG  GAT  CTT  CAA  GAT  GAA  GTT  CAA  AGG  GAG  AGT  ATT  AAT  CTA  CAA  AAA     1268
Gln  Asp  Leu  Gln  Asp  Glu  Val  Gln  Arg  Glu  Ser  Ile  Asn  Leu  Gln  Lys
                    375                     380                     385

CTG  CAG  GCC  CAG  AAG  CAG  CAG  GTG  CAG  GAG  CTC  CTG  GGT  GAA  CTG  GAT     1316
Leu  Gln  Ala  Gln  Lys  Gln  Gln  Val  Gln  Glu  Leu  Leu  Gly  Glu  Leu  Asp
               390                     395                     400

GAG  CAG  AAA  GCC  CAG  CTG  GAG  GAG  CAG  CTC  CAG  GAA  GTC  AGG  AAA  AAG     1364
Glu  Gln  Lys  Ala  Gln  Leu  Glu  Glu  Gln  Leu  Gln  Glu  Val  Arg  Lys  Lys
          405                     410                     415

TGT  GCT  GAG  GAG  GCC  CAG  CTG  ATT  TCT  TCC  CTG  AAA  GCA  GAA  ATA  ACT     1412
Cys  Ala  Glu  Glu  Ala  Gln  Leu  Ile  Ser  Ser  Leu  Lys  Ala  Glu  Ile  Thr
420                     425                     430

AGT  CAA  GAA  TCT  CAG  ATC  TCC  AGT  TAT  GAG  GAA  GAA  CTG  TTG  AAA  GCT     1460
Ser  Gln  Glu  Ser  Gln  Ile  Ser  Ser  Tyr  Glu  Glu  Glu  Leu  Leu  Lys  Ala
435                     440                     445                     450

AGA  GAA  GAA  CTA  AGT  CGC  CTA  CAA  CAA  GAA  ACA  GCA  CAA  TTG  GAA  GAA     1508
Arg  Glu  Glu  Leu  Ser  Arg  Leu  Gln  Gln  Glu  Thr  Ala  Gln  Leu  Glu  Glu
                    455                     460                     465

AGT  GTG  GAG  TCA  GGG  AAG  GCT  CAG  CTG  GAA  CCT  CTT  CAG  CAG  CAC  CTA     1556
Ser  Val  Glu  Ser  Gly  Lys  Ala  Gln  Leu  Glu  Pro  Leu  Gln  Gln  His  Leu
               470                     475                     480

CAA  GAG  TCA  CAA  CAG  GAA  ATC  AGC  TCA  ATG  CAA  ATG  AGA  TTG  GAA  ATG     1604
```

|     |     |     |     |     |     |     |     |     |     |     |     |     |     |     |     |      |
| --- | --- | --- | --- | --- | --- | --- | --- | --- | --- | --- | --- | --- | --- | --- | --- | ---- |
| Gln | Glu | Ser | Gln | Gln | Glu | Ile | Ser | Ser | Met | Gln | Met | Arg | Leu | Glu | Met |      |
|     |     | 485 |     |     |     |     | 490 |     |     |     | 495 |     |     |     |     |      |
| AAA | GAT | CTG | GAA | ACT | GAT | AAT | AAC | CAA | TCA | AAT | TGG | AGC | AGT | AGC | CCA | 1652 |
| Lys | Asp | Leu | Glu | Thr | Asp | Asn | Asn | Gln | Ser | Asn | Trp | Ser | Ser | Ser | Pro |      |
| 500 |     |     |     |     | 505 |     |     |     |     | 510 |     |     |     |     |     |      |
| CAA | AGC | GTT | CTT | GTT | AAT | GGT | GCT | ACA | GAT | TAC | TGT | AGC | CTC | AGC | ACC | 1700 |
| Gln | Ser | Val | Leu | Val | Asn | Gly | Ala | Thr | Asp | Tyr | Cys | Ser | Leu | Ser | Thr |      |
| 515 |     |     |     |     | 520 |     |     |     |     | 525 |     |     |     |     | 530 |      |
| AGC | AGC | AGT | GAA | ACA | GCC | AAC | TTC | AAC | GAA | CAT | GCT | GAA | GGC | CAA | AAC | 1748 |
| Ser | Ser | Ser | Glu | Thr | Ala | Asn | Phe | Asn | Glu | His | Ala | Glu | Gly | Gln | Asn |      |
|     |     |     |     | 535 |     |     |     |     | 540 |     |     |     |     | 545 |     |      |
| AAC | CTA | GAG | TCT | GAA | CCC | ACA | CAC | CAG | GAG | TCC | TCA | GTA | AGA | AGT | AGT | 1796 |
| Asn | Leu | Glu | Ser | Glu | Pro | Thr | His | Gln | Glu | Ser | Ser | Val | Arg | Ser | Ser |      |
|     |     |     | 550 |     |     |     |     | 555 |     |     |     |     | 560 |     |     |      |
| CCT | GAA | ATC | GCA | CCT | TCT | GAT | GTG | ACT | GAT | GAA | AGT | GAG | GCT | GTG | ACT | 1844 |
| Pro | Glu | Ile | Ala | Pro | Ser | Asp | Val | Thr | Asp | Glu | Ser | Glu | Ala | Val | Thr |      |
|     |     | 565 |     |     |     |     | 570 |     |     |     |     | 575 |     |     |     |      |
| GTG | GCT | GGT | AAT | GAG | AAA | GTT | ACT | CCG | AGA | TTT | GAC | GAT | GAC | AAG | CAC | 1892 |
| Val | Ala | Gly | Asn | Glu | Lys | Val | Thr | Pro | Arg | Phe | Asp | Asp | Asp | Lys | His |      |
| 580 |     |     |     |     | 585 |     |     |     |     | 590 |     |     |     |     |     |      |
| TCA | AAA | GAG | GAA | GAT | CCA | TTT | AAT | GTA | GAA | TCA | AGT | TCA | CTG | ACA | GAT | 1940 |
| Ser | Lys | Glu | Glu | Asp | Pro | Phe | Asn | Val | Glu | Ser | Ser | Ser | Leu | Thr | Asp |      |
| 595 |     |     |     |     | 600 |     |     |     |     | 605 |     |     |     |     | 610 |      |
| GCA | GTT | GCA | GAT | ACA | AAC | TTG | GAT | TTT | TCA | CAG | TCT | GAT | CCT | TTT | GTT | 1988 |
| Ala | Val | Ala | Asp | Thr | Asn | Leu | Asp | Phe | Phe | Gln | Ser | Asp | Pro | Phe | Val |      |
|     |     |     |     | 615 |     |     |     |     | 620 |     |     |     |     | 625 |     |      |
| GGC | AGT | GAT | CCT | TTC | AAG | GAT | GAT | CCT | TTT | GGA | AAA | ATT | GAT | CCA | TTT | 2036 |
| Gly | Ser | Asp | Pro | Phe | Lys | Asp | Asp | Pro | Phe | Gly | Lys | Ile | Asp | Pro | Phe |      |
|     |     |     | 630 |     |     |     |     | 635 |     |     |     |     | 640 |     |     |      |
| GGT | GGT | GAC | CCT | TTC | AAA | GGC | TCA | GAT | CCT | TTT | GCG | TCT | GAT | TGC | TTC | 2084 |
| Gly | Gly | Asp | Pro | Phe | Lys | Gly | Ser | Asp | Pro | Phe | Ala | Ser | Asp | Cys | Phe |      |
|     |     |     |     | 645 |     |     |     |     | 650 |     |     |     |     | 655 |     |      |
| TTT | AAG | CAG | ACT | TCT | ACT | GAT | CCT | TTT | ACC | ACT | TCA | AGT | ACG | GAC | CCT | 2132 |
| Phe | Lys | Gln | Thr | Ser | Thr | Asp | Pro | Phe | Thr | Thr | Ser | Ser | Thr | Asp | Pro |      |
|     | 660 |     |     |     |     | 665 |     |     |     |     | 670 |     |     |     |     |      |
| TTC | AGT | GCA | TCC | AGC | AAC | AGC | AGT | AAT | ACA | TCG | GTA | GAA | ACT | TGG | AAG | 2180 |
| Phe | Ser | Ala | Ser | Ser | Asn | Ser | Ser | Asn | Thr | Ser | Val | Glu | Thr | Trp | Lys |      |
| 675 |     |     |     |     | 680 |     |     |     |     | 685 |     |     |     |     | 690 |      |
| CAC | AAT | GAC | CCA | TTT | GCT | CCT | GGT | GGA | ACA | GTT | GTT | GCT | GCA | GCG | AGT | 2228 |
| His | Asn | Asp | Pro | Phe | Ala | Pro | Gly | Gly | Thr | Val | Val | Ala | Ala | Ala | Ser |      |
|     |     |     |     | 695 |     |     |     |     | 700 |     |     |     |     | 705 |     |      |
| GAT | TCA | GCC | ACA | GAC | CCT | TTT | GCT | TCT | GTT | TTC | GGA | AAT | GAA | TCA | TTT | 2276 |
| Asp | Ser | Ala | Thr | Asp | Pro | Phe | Ala | Ser | Val | Phe | Gly | Asn | Glu | Ser | Phe |      |
|     |     |     | 710 |     |     |     |     | 715 |     |     |     |     | 720 |     |     |      |
| GGA | GAT | GGA | TTT | GCT | GAC | TTC | AGC | ACA | TTA | TCA | AAG | GTC | AAC | AAT | GAA | 2324 |
| Gly | Asp | Gly | Phe | Ala | Asp | Phe | Ser | Thr | Leu | Ser | Lys | Val | Asn | Asn | Glu |      |
|     |     | 725 |     |     |     |     | 730 |     |     |     |     | 735 |     |     |     |      |
| GAT | GCT | TTT | AAT | CCT | ACC | ATA | TCA | AGT | TCT | ACC | AGC | AGT | GTG | ACC | ATT | 2372 |
| Asp | Ala | Phe | Asn | Pro | Thr | Ile | Ser | Ser | Ser | Thr | Ser | Ser | Val | Thr | Ile |      |
| 740 |     |     |     |     | 745 |     |     |     |     | 750 |     |     |     |     |     |      |
| GCA | AAA | CCT | ATG | TTA | GAG | GAA | ACA | GCC | AGC | AAG | AGT | GAA | GAT | GTG | CCT | 2420 |
| Ala | Lys | Pro | Met | Leu | Glu | Glu | Thr | Ala | Ser | Lys | Ser | Glu | Asp | Val | Pro |      |
| 755 |     |     |     |     | 760 |     |     |     |     | 765 |     |     |     |     | 770 |      |
| CCA | GCA | CTG | CCG | CCC | AAA | GTT | GGC | ACT | CCA | ACA | AGA | CCT | TGC | CCG | CCA | 2468 |
| Pro | Ala | Leu | Pro | Pro | Lys | Val | Gly | Thr | Pro | Thr | Arg | Pro | Cys | Pro | Pro |      |
|     |     |     |     | 775 |     |     |     |     | 780 |     |     |     |     | 785 |     |      |
| CCC | CCT | GGG | AAA | AGA | CCC | ATC | AAC | AAA | TTG | GAT | TCT | TCT | GAT | CCC | CTT | 2516 |
| Pro | Pro | Gly | Lys | Arg | Pro | Ile | Asn | Lys | Leu | Asp | Ser | Ser | Asp | Pro | Leu |      |
|     |     |     | 790 |     |     |     |     | 795 |     |     |     |     | 800 |     |     |      |
| AAA | CTG | AAT | GAT | CCA | TTT | CAG | CCT | TTC | CCA | GGC | AAT | GAT | AGT | CCC | AAA | 2564 |

```
Lys  Leu  Asn  Asp  Pro  Phe  Gln  Pro  Phe  Pro  Gly  Asn  Asp  Ser  Pro  Lys
          805                      810                     815

GAA  AAA  GAT  CCT  GAT  ATG  TTT  TGT  GAT  CCA  TTC  ACT  TCT  TCT  ACC  ACT        2612
Glu  Lys  Asp  Pro  Asp  Met  Phe  Cys  Asp  Pro  Phe  Thr  Ser  Ser  Thr  Thr
     820                      825                     830

ACC  AAT  AAA  GAG  GCT  GAC  CCA  AGC  AAT  TTT  GCT  AAC  TTC  AGT  GCT  TAT        2660
Thr  Asn  Lys  Glu  Ala  Asp  Pro  Ser  Asn  Phe  Ala  Asn  Phe  Ser  Ala  Tyr
835                      840                     845                     850

CCC  TCT  GAA  GAA  GAT  ATG  ATT  GAA  TGG  GCA  AAA  AGG  GAA  AGT  GAG  CGG        2708
Pro  Ser  Glu  Glu  Asp  Met  Ile  Glu  Trp  Ala  Lys  Arg  Glu  Ser  Glu  Arg
                    855                     860                     865

GAA  GAA  GAA  CAG  AGG  CTT  GCC  AGA  CTA  AAT  CAG  CAG  GAG  CAA  GAA  GAC        2756
Glu  Glu  Glu  Gln  Arg  Leu  Ala  Arg  Leu  Asn  Gln  Gln  Glu  Gln  Glu  Asp
               870                     875                     880

TTG  GAA  CTG  GCC  ATT  GCA  CTT  AGC  AAA  TCT  GAG  ATC  TCA  GAA  GCA  T          2802
Leu  Glu  Leu  Ala  Ile  Ala  Leu  Ser  Lys  Ser  Glu  Ile  Ser  Glu  Ala
          885                     890                     895

GAAGAGTTAT CTGTCCTTTG TCAGCAGTAC AGTGCTCTCT GGAACACTGA AGCTATTTAC                      2862

CATGTGCATC AAACTACCTA TGAGCATGGG ATACAAAGG  TTTGAGATTC CTAGAAATGT                      2922

GACAAAGTC  TAGTTTGTTT TTTTTTTTT  TTTTGGGGGG GGGTGCTATT TCAAATGTGT                      2982

CTTTTATTTT TTCTTCCAAA AGCAGTACCC TAATTAAACG GCTTTGCCTA G                               3033
```

( 2 ) INFORMATION FOR SEQ ID NO:4:

( i ) SEQUENCE CHARACTERISTICS:
        ( A ) LENGTH: 897 amino acids
        ( B ) TYPE: amino acid
        ( D ) TOPOLOGY: linear ( i i ) MOLECULE TYPE: protein ( x i ) SEQUENCE DESCRIPTION: SEQ ID NO:4:

```
Met  Ala  Ala  Ala  Ala  Gln  Leu  Ser  Leu  Thr  Gln  Leu  Ser  Ser  Gly  Asn
1                   5                    10                      15

Pro  Val  Tyr  Glu  Lys  Tyr  Tyr  Arg  Gln  Val  Glu  Ala  Gly  Asn  Thr  Gly
               20                      25                      30

Arg  Val  Leu  Ala  Leu  Asp  Ala  Ala  Ala  Phe  Leu  Lys  Lys  Ser  Gly  Leu
          35                      40                      45

Pro  Asp  Leu  Ile  Leu  Gly  Lys  Ile  Trp  Asp  Leu  Ala  Asp  Thr  Asp  Gly
     50                      55                      60

Lys  Gly  Val  Leu  Ser  Lys  Gln  Glu  Phe  Phe  Val  Ala  Leu  Arg  Leu  Val
65                      70                      75                      80

Ala  Cys  Ala  Gln  Asn  Gly  Leu  Glu  Val  Ser  Leu  Ser  Ser  Leu  Ser  Leu
                    85                      90                      95

Ala  Val  Pro  Pro  Pro  Arg  Phe  His  Asp  Ser  Ser  Pro  Leu  Leu  Thr
                    100                     105                     110

Ser  Gly  Pro  Ser  Val  Ala  Glu  Leu  Pro  Trp  Ala  Val  Lys  Ser  Glu  Asp
          115                     120                     125

Lys  Ala  Lys  Tyr  Asp  Ala  Ile  Phe  Asp  Ser  Leu  Ser  Pro  Val  Asp  Gly
     130                     135                     140

Phe  Leu  Ser  Gly  Asp  Lys  Val  Lys  Pro  Val  Leu  Leu  Asn  Ser  Lys  Leu
145                     150                     155                     160

Pro  Val  Glu  Ile  Leu  Gly  Arg  Val  Trp  Glu  Leu  Ser  Asp  Ile  Asp  His
                    165                     170                     175

Asp  Gly  Lys  Leu  Asp  Arg  Asp  Glu  Phe  Ala  Val  Ala  Met  Phe  Leu  Val
               180                     185                     190

Tyr  Cys  Ala  Leu  Glu  Lys  Glu  Pro  Val  Pro  Met  Ser  Leu  Pro  Pro  Ala
```

|     |     |     | 195 |     |     |     |     | 200 |     |     |     |     | 205 |     |     |
| --- | --- | --- | --- | --- | --- | --- | --- | --- | --- | --- | --- | --- | --- | --- | --- |
| Leu | Val | Pro | Pro | Ser | Lys | Arg | Lys | Thr | Trp | Val | Val | Ser | Pro | Ala | Glu |
|     | 210 |     |     |     |     | 215 |     |     |     |     | 220 |     |     |     |     |
| Lys | Ala | Lys | Tyr | Asp | Glu | Ile | Phe | Leu | Lys | Thr | Asp | Lys | Asp | Met | Asp |
| 225 |     |     |     |     | 230 |     |     |     |     | 235 |     |     |     |     | 240 |
| Gly | Tyr | Val | Ser | Gly | Leu | Glu | Val | Arg | Glu | Thr | Phe | Leu | Lys | Thr | Gly |
|     |     |     |     | 245 |     |     |     |     | 250 |     |     |     |     | 255 |     |
| Leu | Pro | Ser | Ala | Leu | Leu | Ala | His | Ile | Trp | Ser | Leu | Cys | Asp | Thr | Lys |
|     |     |     | 260 |     |     |     |     | 265 |     |     |     |     | 270 |     |     |
| Gly | Cys | Gly | Lys | Leu | Ser | Lys | Asp | Gln | Phe | Ala | Leu | Ala | Phe | His | Leu |
|     |     | 275 |     |     |     |     | 280 |     |     |     |     | 285 |     |     |     |
| Ile | Asn | Gln | Lys | Leu | Ile | Lys | Gly | Ile | Asp | Pro | Pro | His | Ser | Leu | Thr |
|     | 290 |     |     |     |     | 295 |     |     |     |     | 300 |     |     |     |     |
| Pro | Glu | Met | Ile | Pro | Pro | Ser | Asp | Arg | Ser | Ser | Leu | Gln | Lys | Asn | Ile |
| 305 |     |     |     |     | 310 |     |     |     |     | 315 |     |     |     |     | 320 |
| Thr | Gly | Ser | Ser | Pro | Val | Ala | Asp | Phe | Ser | Ala | Ile | Lys | Glu | Leu | Asp |
|     |     |     |     | 325 |     |     |     |     | 330 |     |     |     |     | 335 |     |
| Thr | Leu | Asn | Asn | Glu | Ile | Val | Asp | Leu | Gln | Arg | Glu | Lys | Asn | Asn | Val |
|     |     |     | 340 |     |     |     |     | 345 |     |     |     |     | 350 |     |     |
| Glu | Gln | Asp | Leu | Lys | Glu | Lys | Glu | Asp | Thr | Val | Lys | Gln | Arg | Thr | Ser |
|     |     | 355 |     |     |     |     | 360 |     |     |     |     | 365 |     |     |     |
| Glu | Val | Gln | Asp | Leu | Gln | Asp | Glu | Val | Gln | Arg | Glu | Ser | Ile | Asn | Leu |
|     | 370 |     |     |     |     | 375 |     |     |     |     | 380 |     |     |     |     |
| Gln | Lys | Leu | Gln | Ala | Gln | Lys | Gln | Gln | Val | Gln | Glu | Leu | Leu | Gly | Glu |
| 385 |     |     |     |     | 390 |     |     |     |     | 395 |     |     |     |     | 400 |
| Leu | Asp | Glu | Gln | Lys | Ala | Gln | Leu | Glu | Glu | Gln | Leu | Gln | Glu | Val | Arg |
|     |     |     |     | 405 |     |     |     |     | 410 |     |     |     |     | 415 |     |
| Lys | Lys | Cys | Ala | Glu | Glu | Ala | Gln | Leu | Ile | Ser | Ser | Leu | Lys | Ala | Glu |
|     |     |     | 420 |     |     |     |     | 425 |     |     |     |     | 430 |     |     |
| Ile | Thr | Ser | Gln | Glu | Ser | Gln | Ile | Ser | Ser | Tyr | Glu | Glu | Glu | Leu | Leu |
|     |     | 435 |     |     |     |     | 440 |     |     |     |     | 445 |     |     |     |
| Lys | Ala | Arg | Glu | Glu | Leu | Ser | Arg | Leu | Gln | Gln | Glu | Thr | Ala | Gln | Leu |
|     | 450 |     |     |     |     | 455 |     |     |     |     | 460 |     |     |     |     |
| Glu | Glu | Ser | Val | Glu | Ser | Gly | Lys | Ala | Gln | Leu | Glu | Pro | Leu | Gln | Gln |
| 465 |     |     |     |     | 470 |     |     |     |     | 475 |     |     |     |     | 480 |
| His | Leu | Gln | Glu | Ser | Gln | Gln | Glu | Ile | Ser | Ser | Met | Gln | Met | Arg | Leu |
|     |     |     |     | 485 |     |     |     |     | 490 |     |     |     |     | 495 |     |
| Glu | Met | Lys | Asp | Leu | Glu | Thr | Asp | Asn | Asn | Gln | Ser | Asn | Trp | Ser | Ser |
|     |     |     | 500 |     |     |     |     | 505 |     |     |     |     | 510 |     |     |
| Ser | Pro | Gln | Ser | Val | Leu | Val | Asn | Gly | Ala | Thr | Asp | Tyr | Cys | Ser | Leu |
|     |     | 515 |     |     |     |     | 520 |     |     |     |     | 525 |     |     |     |
| Ser | Thr | Ser | Ser | Ser | Glu | Thr | Ala | Asn | Phe | Asn | Glu | His | Ala | Glu | Gly |
|     | 530 |     |     |     |     | 535 |     |     |     |     | 540 |     |     |     |     |
| Gln | Asn | Asn | Leu | Glu | Ser | Glu | Pro | Thr | His | Gln | Glu | Ser | Ser | Val | Arg |
| 545 |     |     |     |     | 550 |     |     |     |     | 555 |     |     |     |     | 560 |
| Ser | Ser | Pro | Glu | Ile | Ala | Pro | Ser | Asp | Val | Thr | Asp | Glu | Ser | Glu | Ala |
|     |     |     |     | 565 |     |     |     |     | 570 |     |     |     |     | 575 |     |
| Val | Thr | Val | Ala | Gly | Asn | Glu | Lys | Val | Thr | Pro | Arg | Phe | Asp | Asp | Asp |
|     |     |     | 580 |     |     |     |     | 585 |     |     |     |     | 590 |     |     |
| Lys | His | Ser | Lys | Glu | Glu | Asp | Pro | Phe | Asn | Val | Glu | Ser | Ser | Ser | Leu |
|     |     | 595 |     |     |     |     | 600 |     |     |     |     | 605 |     |     |     |
| Thr | Asp | Ala | Val | Ala | Asp | Thr | Asn | Leu | Asp | Phe | Phe | Gln | Ser | Asp | Pro |
|     | 610 |     |     |     |     | 615 |     |     |     |     | 620 |     |     |     |     |

| | | | | | | | | | | | | | | |
|---|---|---|---|---|---|---|---|---|---|---|---|---|---|---|
| Phe 625 | Val | Gly | Ser | Asp | Pro 630 | Phe | Lys | Asp | Pro 635 | Phe | Gly | Lys | Ile | Asp 640 |
| Pro | Phe | Gly | Gly | Asp 645 | Pro | Phe | Lys | Gly | Ser 650 | Asp | Pro | Phe | Ala | Ser 655 | Asp |
| Cys | Phe | Phe | Lys 660 | Gln | Thr | Ser | Thr | Asp 665 | Pro | Phe | Thr | Thr | Ser 670 | Ser | Thr |
| Asp | Pro | Phe 675 | Ser | Ala | Ser | Ser | Asn 680 | Ser | Ser | Asn | Thr | Ser 685 | Val | Glu | Thr |
| Trp | Lys 690 | His | Asn | Asp | Pro | Phe 695 | Ala | Pro | Gly | Gly | Thr 700 | Val | Val | Ala | Ala |
| Ala 705 | Ser | Asp | Ser | Ala | Thr 710 | Asp | Pro | Phe | Ala | Ser 715 | Val | Phe | Gly | Asn | Glu 720 |
| Ser | Phe | Gly | Asp | Gly 725 | Phe | Ala | Asp | Phe | Ser 730 | Thr | Leu | Ser | Lys | Val 735 | Asn |
| Asn | Glu | Asp | Ala 740 | Phe | Asn | Pro | Thr | Ile 745 | Ser | Ser | Ser | Thr | Ser 750 | Ser | Val |
| Thr | Ile | Ala 755 | Lys | Pro | Met | Leu | Glu 760 | Glu | Thr | Ala | Ser | Lys 765 | Ser | Glu | Asp |
| Val | Pro 770 | Pro | Ala | Leu | Pro | Pro 775 | Lys | Val | Gly | Thr | Pro 780 | Thr | Arg | Pro | Cys |
| Pro 785 | Pro | Pro | Pro | Gly | Lys 790 | Arg | Pro | Ile | Asn | Lys 795 | Leu | Asp | Ser | Ser | Asp 800 |
| Pro | Leu | Lys | Leu | Asn 805 | Asp | Pro | Phe | Gln | Pro 810 | Phe | Pro | Gly | Asn | Asp 815 | Ser |
| Pro | Lys | Glu | Lys 820 | Asp | Pro | Asp | Met | Phe 825 | Cys | Asp | Pro | Phe | Thr 830 | Ser | Ser |
| Thr | Thr | Thr 835 | Asn | Lys | Glu | Ala | Asp 840 | Pro | Ser | Asn | Phe | Ala 845 | Asn | Phe | Ser |
| Ala | Tyr 850 | Pro | Ser | Glu | Glu | Asp 855 | Met | Ile | Glu | Trp | Ala 860 | Lys | Arg | Glu | Ser |
| Glu 865 | Arg | Glu | Glu | Glu | Gln 870 | Arg | Leu | Ala | Arg | Leu 875 | Asn | Gln | Gln | Glu | Gln 880 |
| Glu | Asp | Leu | Glu | Leu 885 | Ala | Ile | Ala | Leu | Ser 890 | Lys | Ser | Glu | Ile | Ser 895 | Glu |
| Ala | | | | | | | | | | | | | | | |

DNA ENCODING HUMAN AND MURINE EPS15, A SUBSTRATE FOR THE EPIDERMAL GROWTH FACTOR RECEPTOR

CROSS REFERENCE TO RELATED APPLICATIONS

The present invention is a continuation-in-part of U.S. application Ser. No. 07/935,311, filed Aug. 25, 1992, now U.S. Pat. No. 5,378,809 which is incorporated by reference herein in its entirety.

FIELD OF THE INVENTION

The present invention relates to substrates for the epidermal growth factor receptor kinass, polynucleotides encoding the substrates, and methods for using the substrates.

BACKGROUND OF THE INVENTION

The cellular machinery involved in mitogenesis is complex, and not fully understood. In general, receptors present on the cell surface bind growth factors, resulting in an activated receptor. In particular, the receptors of interest are endowed with intrinsic tyrosine kinass activity, and are known as tyrosine kinass receptors or TKRs. The activated receptors, in turn, phosphorylate intracellular substrates. These phosphorylated substrates are responsible for a series of events that leads to cell division. This process is generally referred to as "mitogenic signal transduction." The molecular machinery involved in this process is considered to be the "mitogenic signaling pathway."

Growth factors and hormones exert pleiotropic effects on cellular functions, including mitogenic stimulation and modulation of differentiation and metabolism (Ullrich et al., *Cell* 61: 203–212 (1990); Aaronson, *Science* 254: 1146–1153 (1991)). In many cases, these effects are mediated by the interaction of growth factors with cell surface tyrosine kinass receptors (TKRs), resulting in enhanced receptor catalytic activity and tyrosine phosphorylation of intracellular substrates (Ullrich et al., supra; Aaronson, supra). Data regarding the nature of these second messenger systems is still scanty, although some molecules which associate and/or are tyrosine phosphorylated by TKRs have been identified. These include the γ isozyme of phospholipase C (PLC-γ) (Margolis et al., *Cell* 57: 1101–1107 (1989); Meisenhelder et al., *Cell* 57: 1109–1122 (1989); Wahl et al., *Mol. Cell. Biol.* 9: 2934–2943 (1989)); the p21ras GTPase activating protein (GAP) (Molloy et al., *Nature* 342: 711–714 (1989); Kaplan et al., *Cell* 61: 125–133 (1990); Kazlauskas et al., *Science* 247: 1578–1581 (1990)); the raf serine-threonine kinase (Morrison et al., *Proc. Natl. Acad. Sci. USA* 85: 8855–8859 (1988); Morrison et al., *Cell* 58: 649–657 (1989)); the p85 subunit of the phosphatidylinositol 3-kinase (PtdIns-3K); (Coughlin et al., *Science* 243: 1191–1194 (1989); Kazlauskas et al., *Cell* 58: 1121–1133 (1989); Varticovski et al., *Nature* 342: 699–702 (1989); Ruderman et al., *Proc. Natl. Acad. Sci. USA* 87: 1411–1415 (1990); Escobedo et al., *Cell* 65: 75–82 (1991); Skolnik et al., *Cell* 65: 83–90 (1991); Otsu et al., *Cell* 65: 91–104 (1991)) and some cytoplasmic tyrosine kinases (Gould et al., *Mol. Cell. Biol.* 5: 3345–3356 (1988); Kypta et al., *Cell* 62: 481–492 (1990)). These signaling molecules are thought to mediate at least in part the mitogenic effects of TKRs (Ullrich et al., *Cell* 61: 203–212 (1990); Aaronson, *Science* 254: 1146–1153 (1991)).

However, the epidermal growth factor (EGF) receptor (EGFR) does not appear to efficiently interact with known second messenger systems (Fazioli et al., *Mol. Cell. Biol.* 11: 2040–2048 (1991); Segatto et al., *Mol. Cell. Biol.* 11: 3191–3202 (1991)). Thus, there is a need to ascertain the mechanism by which the EGFR functions in mitogenesis, and a particular need to identify and characterize the substrate (if any) of the EGFR.

Errors which occur in the mitogenic signaling pathway, such as alterations in one or more elements of that pathway, are implicated in malignant transformation and cancer. It is believed that in at least some malignancies, interference with abnormal mitogenic signal transduction could cause reversion of cells to a normal phenotype.

In addition, reagents useful in identifying molecular components of the mitogenic signaling pathway would find utility as tumor markers for therapeutic, diagnostic, and prognostic purposes. Furthermore, identification of how such components differ from normal components in malignant tissue might be of significant value in understanding and treating such malignancies. Alterations of the EGFR mitogenic signal transduction pathway have been described in several human tumors. Accordingly, substrates of the EGFR are of particular interest.

Finally, there is a need to identify reagents that can be used to determine the tyrosine kinase activity of particular samples of biological origin. Determination of the tyrosine kinase activity of samples could have value in the therapy, diagnosis, and prognosis of neoplasia and other disorders connected with abnormal mitogenic signaling pathways.

It is therefore an object of the present invention to provide reagents and methods useful in identifying components of the mitogenic signal transduction pathway, for determining tyrosine kinase activity of samples, and for determining how particular components of the pathway in abnormal tissue differ from normal components. In particular, it is an object of the invention to provide reagents and methods that relate to the EGFR substrate(s).

SUMMARY OF THE INVENTION

A method is disclosed which allows direct cloning of intracellular substrates for tyrosine kinase receptors (TKRs). By applying this technique to the study of the epidermal growth factor (EGF) receptor (EGFR) signaling pathway, a cDNA designated eps15 has been isolated. The structural features of the deduced eps15 gene product allow its subdivision into three domains. Domain I contains signatures of a regulatory domain, including a candidate tyrosine phosphorylation site and EF-hand type calcium-binding domains. Domain II presents the characteristic heptad repeats of coil-coiled rod-like proteins. Domain III displays a repeated aspartic acid-proline-phenylalanine motif reminiscent of a consensus sequence of several methylases. Eps15 does not bear the Src homology 2 (SH2) and Src homology 3 (SH3) domains, characteristic signatures of TKR substrates. Antibodies specific to the eps15 gene product recognize a protein of 142 kDa and a minor component of 155 kDa, which are phosphorylated on tyrosine following EGFR activation by EGF invivo. In addition, phosphorylation of the eps15 gene product must be relatively receptor-specific, since erbB-2, an EGFR-related kinase, phosphorylates it very inefficiently. By employing chimeric molecules between EGFR and gp185$^{erbB-2}$, the region of the EGFR responsible for the differential phosphorylation of eps15 could be mapped to its juxtamembrane region. Overexpression of eps15 is sufficient to transform NIH-3T3 cells, thus implicating the eps15 gene product in the regulation of mitogenic signals.

Thus, one aspect of the present invention is isolated or purified polynucleotide encoding eps15 substrate of the epidermal growth factor receptor, preferably mammalian eps15, and more preferably human eps15. The sequence can include polynucleotide coding for mouse eps15, including polynucleotide encoding the amino acid sequence of SEQ ID NO:4, the DNA sequence of SEQ ID NO:3, and a mRNA transcript of SEQ ID NO:3. Also encompassed within the scope of the invention is sequence coding for human eps15 that includes the polynucleotide encoding the amino acid sequence of SEQ ID NO:2, the DNA sequence of SEQ ID NO:1, and a mRNA transcript of SEQ ID NO:1. Moreover, the invention includes an antisense oligonucleotide and a triple helix probe capable of blocking expression of the eps15 gene product, preferably including at least 15 nucleotides.

The invention further comprises isolated or purified eps15, preferably mammalian eps15, and more preferably human eps15. Included within the scope of the invention is mouse eps15, which can have the amino acid sequence of SEQ ID NO:4. The human eps15 advantageously includes the amino acid sequence of SEQ ID NO:2. The concentration of the isolated or purified eps15 is preferably at least 1 μg/ml.

Another aspect of the invention is isolated or purified antibody to eps15, including both monoclonal and polyclonal antibody.

Yet another aspect of the invention is a construct including a vector and sequence encoding the eps15 substrate; and a host transformed therewith.

Furthermore, the invention features a method for enhancing the mitogenic response of cells to mitogenic factors, including the step of administering to the cells an effective mitogenic-response enhancing amount of eps15.

Another aspect of the invention is a method for determining TKR tyrosine kinase activity in a biological sample, including the steps of combining eps15 with the sample, and measuring tyrosine phosphorylation of the eps15 by the TKR tyrosine kinase in the sample.

The invention also provides a method for determining eps15 in a sample, including the steps of contacting the sample with antibody to eps15, such that an immunological complex forms between eps15 and the antibody, and detecting the formation of the immunological complex.

DETAILED DESCRIPTION OF THE INVENTION

Figure 1:
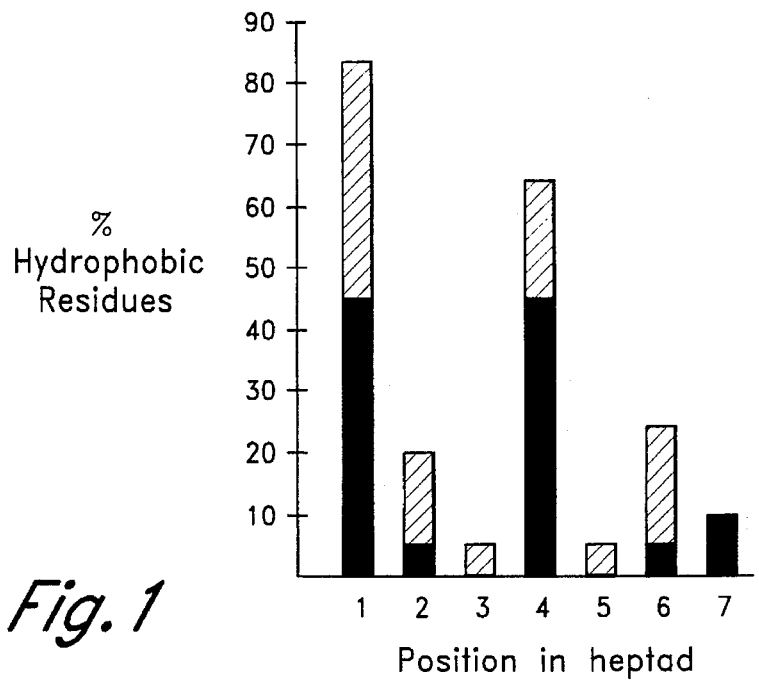
FIG. 1 presents an analysis of the heptads in the second of the three structural domains charaterizing eps15 deduced from the the mouse cDNA. The amino acid position in each heptad is plotted against the frequency of hydrophobic residues at each position. Hydrophobicity was evaluated according to Kyte and Doolittle. (Kyte and Doolittle, *J. Mol. Biol.* 157: 105–132 (1982)). Leucine residues are represented by closed boxes, other hydrophobic residues by dashed boxes.

The present invention includes the discovery of a novel epidermal growth factor (EGF) receptor (EGFR) substrate which is called eps15 (EGFR pathway substrate), together with complete cDNA and deduced protein sequences for the murine eps15 (SEQ ID NOS:3 and 4, respectively) and cDNA and deduced protein sequence for the human eps15 (SEQ ID NOS:1 and 2, respectively). The protein sequences are referred to as "deduced" sequences simply because they were determined from the nucleotide sequence, rather than from analysis of purified natural protein.

In addition, the present invention provides methodology for isolating cDNA and protein sequences of other species; antibodies which recognize the proteins encoded by the cDNAs; expression vectors for producing eps15 in prokaryotic or eukaryotic cells; cell lines expressing eps15; and assays using the antibodies, cDNA sequences, and proteins.

The sequences falling within the scope of the present invention are not limited to the specific sequences described, but include functional fragments thereof, that is, fragments that function in substantially the same way as do the specific sequences described. Functional polynucleotide fragments having at least about 60 nucleotides, advantageously at least about 30 nucleotides, and preferably at least about 15 nucleotides are contemplated. Regarding functional polypeptide fragments, those having at least about 20 amino acid residues, advantageously at least about 10 amino acid residues, and preferably at least about 5 amino acid residues are considered. Moreover, the invention includes conservative variants of the specific proteins described, i.e., substituents incorporating conservative changes for any of the amino acid residues provided herein. Further, to accommodate codon degeneracy, the invention encompasses any DNA sequence encoding the proteins of the present invention.

The eps15 proteins, polynucleotide sequences, constructs, vectors, clones, and other materials comprising the present invention can advantageously be in isolated form. As used herein, the term "isolated" denotes that the material has been removed from its original environment (e.g., the natural environment if it is naturally occurring). For example, a naturally-occurring polynucleotide or polypeptide present in a living animal is not isolated, but the same polynucleotide or polypeptide, separated from some or all of the coexisting materials in the natural system, is isolated.

It is also advantageous that the sequences and other materials comprising the invention be in purified form. The term "purified" does not require absolute purity; rather, it is intended as a relative definition. Purification of starting material or natural material means that the concentration of the material is at least about 2, 5, 10, 100 or 1000 times its original concentration (for example), advantageously 0.01% by weight, preferably at least about 0.1% by weight. Purified preparations of about 0.5%, 1%, 5%, 10% and 20% by weight are also contemplated.

A. Overview

Two lines of evidence indicate that the EGF receptor is not very efficient at coupling with known second messenger systems. There is a low stoichiometry of tyrosine phosphorylation (~1% of the total pools), of PLC-γ, and GAP weak induction of PIP2 breakdown, and very little phosphorylation/activation of raf or activation of PtdIns-3K by EGFR, even when overexpressed at levels of approximately 2×10$^6$ receptors/cell (Fazioli et al., *Mol. Cell Biol.* 11: 2040–2048 (1991)). In addition, a mitogenesis-incompetent mutant of the EGFR (EGFR Δ660–667 Segatto et al., *Mol. Cell Biol.* 11: 3191–3202 (1991)) did not show any decreased ability to phosphorylate PLC-γ or GAP, or to induce PIP2 breakdown as compared to the wild type EGFR (Segatto et al., *Mol. Cell Biol.* 11: 3191–3202 (1991)). This strongly indicated the existence of alternative effector pathways for mitogenic signal transduction by EGFR.

Characterization of EGFR-activated pathways requires the identification of novel proteins that are tyrosine phosphorylated following stimulation of this receptor kinase. The present invention utilized a novel approach to the cloning of cDNAs coding for EGFR substrates, as disclosed in Fazioli et al., *J. Biol. chem.* 267: 5155–5157 (1992) and Fazioli et al., *Oncogene* 8: 1335–1345 (1993), which are hereby incorporated by reference. The approach relies on batch purification of the entire set of proteins that are phosphorylated on tyrosine following EGFR activation and generation of antisera directed against the entire pool of purified proteins. These sera can be used to immunologically characterize various substrates or for expression screening of cDNA libraries.

B. Identification of Murine cDNA Encoding eps15

Antibodies to phosphotyrosine were used to isolate proteins that were tyrosine-phosphorylated upon EGF stimulation of NIH-3T3 murine fibroblasts overexpressing the EGFR (NIH-EGFR cells), as discussed in Example 1. A strategy was developed that allowed direct cloning of the cDNAs encoding several of these proteins. Briefly, two polyclonal sera were generated using the entire purified pool of phosphotyrosine (pTyr)-containing proteins as an immunogen (Fazioli et al., *J. Biol. Chem.* 267: 5155–5157 (1992)). These antibodies were used for expression screening of cDNA libraries, as reported in greater detail in Examples 1 and 2.

A novel cDNA isolated by this method was sequenced as described in Example 3, and the encoded protein was designated eps15. The nucleotide sequence of the eps15 cDNA is presented herein as SEQ ID NO:3. The deduced amino acid sequence, given herein as SEQ ID NO:4, describes a protein bearing a candidate tyrosine phosphorylation site but, surprisingly, no Src homology 2 (SH2) or Src homology 3 (SH3) domains which are the characteristic hallmarks of TKR substrates. Antibodies generated against the cDNA protein product in accordance with Example 4 recognized in NIH-EGFR cells a 142 kDa protein and a less abundant 155 kDa protein, both of which were phosphorylated on tyrosine residues following treatment of intact cells with EGF.

C. Features and Properties of eps15 Protein

The amino acid sequence deduced from the single eps15 ORF provides a 897 amino acid protein with a calculated molecular weight of approximately 98 kDa.

The features of the deduced polypeptide indicated the presence of three structural domains. Domain I (spanning between amino acid positions 9–314) consisted of three imperfect repeats of 95–97 amino acids, with a 55–60% overall degree of conservation. The second repeat included a tyrosine, at position 132, flanked by the consensus sequence for putative tyrosine phosphorylation sites (Bairoch, *Nucleic Acids. Res.* 20: 2013–2018 (1992); Hunter, *J. Biol. Chem.* 257: 4843–4848 (1982)). This tyrosine residue was conserved in the first and third repeat of Domain I, although it was not flanked by the phosphorylation consensus. The second and third repeat also contained consensus sequences for calcium-binding domains of the EF-hand type (Bairoch, *Nucleic Acids. Res.* 20: 2013–2018 (1992); Heizmann et al., *Trends Biochem. Sci.* 16: 98–103 (1991)) at positions 173–185 and 236–248, respectively.

Figure 2:
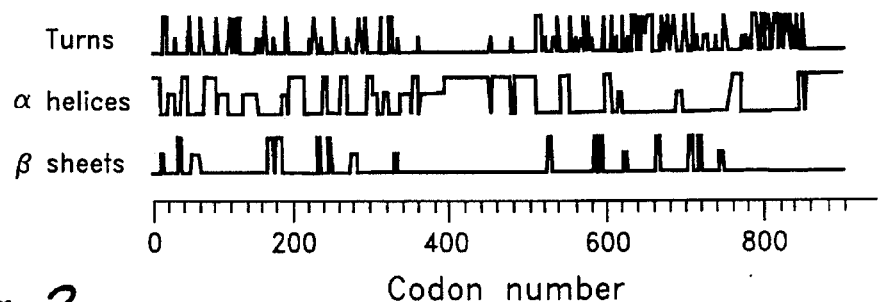
FIG. 2 provides a secondary structure analysis of the eps15 protein product deduced from the mouse cDNA. Scores were calculated with the Chou-Fassman algorithm. (Chou and Fassman, *Adv. Enzymol. Relat. Areas Mol. Biol.* 47: 45–148 (1978)). Turns, alpha helices, and beta sheets are graphed against amino acid number.

Domain II (amino acid positions 335–502) presented the typical features of an α-helical coiled-coil structure, common to several cytoskeleton-related proteins. The requisite for the formation of a coiled-coil α-helix is the presence of heptad repeats, in which the first and fourth positions usually contain hydrophobic amino acid residues (McLachlan et al., *J. Mob. Biol.* 164: 605–626 (1983)). Domain II of eps15 was composed of 24 contiguous heptads whose positions 1 and 4 were markedly biased in favor of apolar amino acids, in particular leucine. FIG. 1. In addition, Domain II contained only 2 glycines and 1 proline (1.8% of the total residues, as opposed to 11.8% in the entire eps15) which are both strong α-helix breakers. Secondary structure analysis (FIG. 2) indicated that this region has the potential to form an α-helix.

Figure 3:
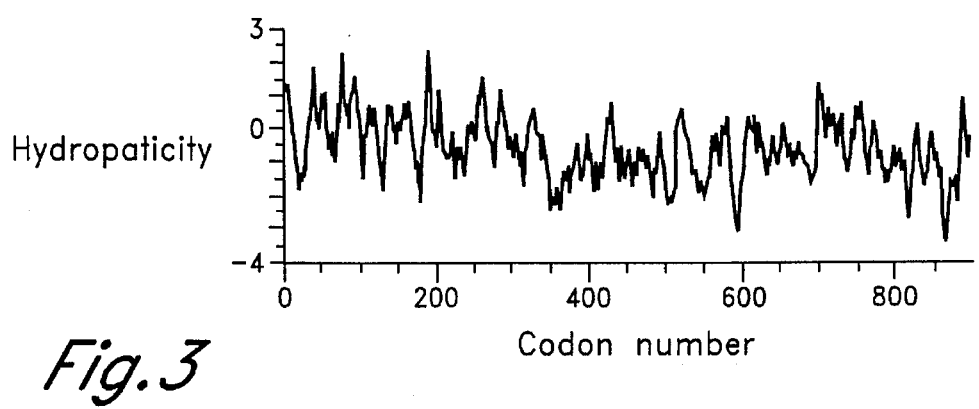
FIG. 3 profiles the hydropaticity of eps15 deduced from the mouse cDNA. Values were calculated according to Kyte and Doolittle (Kyte and Doolittle, supra) on a window of 10 amino acids with equal weights. Positive values indicate hydrophobicity, negative values hydrophilicity. Hydropaticity is diagrammed against amino acid number.

Domain III (amino acids 598–842) was characterized by the repetition of a three amino acid motif, aspartic acid-proline-phenylalanine (DPF repeat); thirteen perfect DPFs and eight imperfect repeats (DXF, DPX and XPF) were identified. A hydropaticity plot of eps15 (FIG. 3) did not reveal any long stretch of hydrophobic amino acids that would qualify as a transmembrane domain, nor any signal peptide.

Remarkably, no Src homology 2 (SH2) or Src homology 3 (SH3) domains, which are characteristic signatures of TKR substrates (Koch et al., *Science* 252: 668–674 (1991)), were identifiable. Src homology (SH) regions 2 and 3 are noncatalytic regions conserved among substrates regulated by TKRs. The SH2 domains of these substrates bind activated TKRs and other tyrosine phosphorylated proteins, thus suggesting a role for SH2 in the mediation of protein-protein interactions. SH3 sequences are implicated in acting together with SH2 to modulate interactions with the cytoskeleton and membrane. The lack of SH2 and SH3 domains suggests that eps15 exploits other novel mechanisms for regulating protein-protein interactions during signal transduction.

D. Obtaining of Human cDNA for eps15

The present invention includes partial and complete human cDNA sequences and human genomic DNA sequences for eps15. A partial human eps15 sequence was obtained by PCR amplification from a human cDNA library using short sequences of the mouse eps15 cDNA as primers. This procedure is explained in more detail in Example 5.

A resultant PCR product containing partial sequence for human eps15 was used as a probe to identify a human cDNA clone potentially corresponding to a full-length transcript. See Example 6. The cDNA sequence for this human eps15 clone is set forth herein as SEQ ID NO:1. The deduced protein sequence of the human eps15 was 896 amino acids in length and included the entire open reading frame corresponding to the mouse eps15 cDNA. The human amino acid sequence displayed 90% identity to the mouse sequence. The peptide sequence for human eps15 is included herein as SEQ ID NO:2.

Although the described human eps15 cDNA clone may not be full length, such a clone can be obtained using well known methodology. For example, antibodies against the expression product of the human cDNA sequence of SEQ ID NO:1 can be used for expression screening of a cDNA library. These experiments can employ the techniques set forth in Example 4 to generate polyclonal antibodies against human eps15, and then candidate clones can be identified as set forth in Example 2 and characterized by sequencing as set forth in Example 3.

Additionally, conventional biochemical techniques permit use of a partial or complete cDNA clone as a probe to identify a cDNA corresponding to a full-length transcript or a genomic clone having the complete eps15 gene, including regulatory and promoter regions, exons, and introns.

One general approach for obtaining a complete cDNA sequence or genomic DNA sequence corresponding to the human eps15 gene is as follows:

1. Label a human eps15 cDNA and use it as a probe to screen a human lambda phage cDNA library or a human plasmid cDNA library.
2. Identify colonies containing clones related to the probe cDNA and purify them by known purification methods.
3. Nucleotide sequence the ends of the newly purified clones to identify full length sequences.
4. Perform complete nucleotide sequencing of putative full length clones by Exonuclease III digestion or primer walking using art-known means. Northern blots of mRNA from various tissues using at least part of the clone as a probe can be performed to check the size of the mRNA against that of the purported full. length cDNA.

More particularly, all or part of the DNA sequence of SEQ ID NO:1 may be used as a probe to identify cDNA clones containing the full length cDNA sequence. The partial sequence of SEQ ID NO:1, or portions thereof, can be nick-translated or end-labelled with $^{32}P$ using polynucleotide kinase and labelling methods known to those with skill in the art (Basic Methods in Molecular Biology, L. G. Davis, M. D. Dibner, and J. F. Battey, ed., Elsevier Press, N.Y. 1986). A lambda library can be directly screened with the labelled cDNA probe, or the library can be converted en masse to pBluescript® (Stratagene, La Jolla, Calif.) to facilitate bacterial colony screening. Both methods are well known in the art.

Briefly, filters with bacterial colonies containing the library in pBluescript® or bacterial lawns containing lambda plaques are denatured and the DNA is fixed to the filters. The filters are hybridized with the labelled probe using hybridization conditions described by Davis et al. All or part of SEQ ID NO:1, cloned into lambda or pBluescript®, can be used as a positive control to assess background binding and to adjust the hybridization and washing stringencies necessary for accurate clone identification. The resulting autoradiograms are compared to duplicate plates of colonies or plaques, where each exposed spot corresponds to a positive colony or plaque. The colonies or plaques are selected, expanded, and the DNA is isolated from the colonies for further analysis and sequencing.

Positive cDNA clones in phage lambda may be analyzed to determine the amount of additional sequence they contain using PCR with one primer from the sequence obtained from SEQ ID NO:1 and the other primer from the vector. Clones with a larger vector-insert PCR product than the original clone are analyzed by restriction digestion and DNA sequencing to determine whether they contain an insert of the same size or similar as the mRNA size on a Northern blot.

Once one or more overlapping cDNA clones are identified, the complete sequence of the clones can be determined. The preferred method is to use Exonuclease III digestion (McCombie et al., *Methods* 3: 33–40 (1991)). A series of deletion clones is generated, each of which is sequenced. The resulting overlapping sequences are assembled into a single contiguous sequence of high redundancy (usually three to five overlapping sequences at each nucleotide position), resulting in a highly accurate final sequence.

A similar screening and clone selection approach can be applied to obtaining cosmid or lambda clones from a genomic DNA library (Kirkness et al., *Genomics* 10: 985–995 (1991)). Although the process is much more laborious, these genomic clones can also be sequenced in their entirety. A shotgun approach is preferred to sequencing clones with inserts longer than 10 kb (genomic cosmid and lambda clones). In shotgun sequencing, the clone is randomly broken into many small pieces, each of which is partially sequenced. The sequence fragments are then aligned via computer to produce a final contiguous sequence with high redundancy. An intermediate approach to obtaining genomic DNA sequence is to sequence just the promoter region and the intron-exon boundaries and to estimate the size of the introns by restriction endonuclease digestion.

E. Expression of eps15 Gene

Following isolation and characterization of the eps15 gene, it is routine to express that gene in a recombinant organism to obtain significant amounts of eps15. One example of a suitable expression vector and host is set forth in Example 4. Alternatively, the DNA encoding eps15 can be inserted into other conventional host organisms and expressed. The organism can be a bacterium, yeast, cell line, or multicellular plant or animal. The literature is replete with examples of suitable host organisms and expression techniques. For example, naked polynucleotide (DNA or mRNA) can be injected directly into muscle tissue of mammals, wherein it is expressed. This methodology can be used to deliver the polynucleotide and, therefore, the resulting polypeptide translation product to the animal, or to generate an inmmune response against a foreign polypeptide (Wolff et al., *Science* 247: 1465 (1990); Felgner et al., *Nature* 349: 351 (1991)). Alternatively, the coding sequence, together with appropriate regulatory regions (i.e., a construct), can be inserted into a vector, which is then transfected into a cell. The cell (which may or may not be part of a larger organism) then expresses the polypeptide.

F. In vivo Transcription of eps15

In order to assess the expression of mRNA encoded by the murine eps15 gene, we performed Northern blot analysis of poly(A)+RNA extracted from NIH-3T3 cells using the pl 15 insert as a probe. Two major bands of ~3.3 and ~6.0 kb were detected. The size of the smaller band was in agreement with that of the eps15 cDNA clone. The nature of the 6.0 kb band was not resolved. It is unlikely that the band represents a related species since hybridization was performed under high stringency conditions. Thus, it most likely represents a partially processed precursor or an alternatively spliced form of the transcript.

G. Assays for Detecting eps15

Antibodies generated against the eps15 polypeptide can be obtained by direct injection of the naked polynucleotide into an animal (Wolff et al., *Science* 247: 1465 (1990)) or by administering the polypeptide to an animal, as explained in Example 4. The antibody so obtained will then bind the polypeptide itself. In this manner, even a sequence encoding only a fragment of eps15 can be used to generate antibodies binding the entire native polypeptide.

Antibodies generated in accordance with Example 4 can be used in standard immunoassay formats to detect the presence and/or amount of eps15 in a sample. Such assays can comprise competitive or noncompetitive assays. Radioimmunoassays, ELISAs, Western Blot assays, immunohistochemical assays, immunochromatographic assays, and other conventional assays are expressly contemplated. Furthermore, polyclonal antibodies against human or other eps15 can be readily generated using the techniques of Example 4, and monoclonal antibodies to any form of eps15 can be generated using well-known methods. All of these antibodies can be used in assays of the present invention. The assays and the antibodies discussed herein form an embodiment of this invention.

H. Detection of TKR Kinase Activity

In many instances, it is important to know the TKR tyrosine kinase activity of a sample. The present invention provides a ready method by which such activity can be determined. As discussed in more detail infra eps15 is tyrosine phosphorylated by the EGFR as well as by other tyrosine kinase receptors. This ability of TKRs to phosphorylate eps15 is exploited to measure the presence of TKRs in a sample.

Briefly, one method for such measurement is to contact a sample with eps5, add radiolabeled γ-ATP to the sample and then measure the extent to which the radiolabel is incorporated into the eps15. Anti-eps15 antibodies may be used in the final step of the assay to capture eps15 for measurement of phosphorylation. Such assays are disclosed in more detail in Examples 9 and 10.

I. Differential Phosphorylation of eps15 by the EGFR and erbB-2 Kinase

As discussed in more detail herein, eps15 is tyrosine phosphorylated by the EGFR kinase and much less efficiently by the highly related $gp185^{erbB}$-2 kinase, an unexpected finding in light of the high degree of homology between these two kinases.

The availability of anti-eps15 antibodies permitted testing of the specificity of eps15 phosphorylation by the EGFR and erbB-2 kinases. Tyrosine phosphorylation of the major species of the eps15 gene product, $p142^{eps15}$, was measured. Two mass populations of NIH-3T3 cells transfected either with EGFR or with the EGFR/erbB-2 chimera containing the extracellular domain of EGFR and the intracellular domain of erbB-2 were utilized (Fazioli et al., *Mol. Cell. Biol.* 11: 2040–2048 (1991); Lee et al., *EMBO J.* 8: 167–173 (1989); Lehvaslaiho et al., *EMBO J.* 8: 159–166 (1989); Lonardo et al., *New Biol.* 2: 992–1003 (1990)). The NIH-EGFR and NIH-EGFR/erbB-2 lines expressed comparable number of receptors and exhibited similar affinity for EGF binding, thus allowing rigorous quantitative analysis of the in vitro phosphorylation events triggered by EGF stimulation.

EGF treatment of NIH-EGFR/erbB-2 cells resulted in little if any tyrosine phosphorylation of $p142^{eps15}$, although it induced readily detectable autophosphorylation of the chimeric receptor and phosphorylation of a number of other intracellular proteins. Conversely, EGF stimulation of NIH-EGFR promptly triggered $p142^{eps15}$ tyrosine phosphorylation. The differential response of NIH-EGFR and NIH-EGFR/erbB-2 could not be ascribed to intrinsic differences in the two cell lines, since PDGF stimulation was able to elicit $p142^{eps15}$ phosphorylation in both of them. It was concluded, therefore, that the erbB-2 kinase is much less efficient than the EGFR at stimulating tyrosine phosphorylation of $p142^{eps15}$.

A panel of chimeric molecules constructed from regions of the EGFR and erbB-2 kinase was employed to map the portion(s) of these receptors responsible for the differential tyrosine phosphorylation of eps15 by EGFR and erbB-2. The chimerae were engineered by substituting domains of $gp185^{erbB-2}$ for the corresponding regions of the EGFR and have been previously described and characterized (Di Fiore et al., *Cell* 51: 1063–1070 (1987); Di Fiore et al., *Mol. Cell. Biol.* 10: 2749–2756 (1990); Di Fiore et al., *Science* 248: 79–83 (1990); Segatto et al., *Mol. Cell. Biol.* 11: 3191–3202 (1991)). An EGFR/erbB-$2^{COOH}$ chimera, in which the carboxyl terminal (COOH) domain of $gp185^{erbB-2}$ was substituted for the COOH domain of EGFR, was able to phosphorylate eps15 comparably to the wild type EGFR. Conversely, the substitution of the tyrosine kinase (TK) region of $gp185^{erbB-2}$ into EGFR (EGFR/erbB-$2^{TK}$) yielded a molecule which was severely impaired in its ability to phosphorylate eps15. Further mapping showed that the substitution of the first ~150 amino acid of $gp185^{erbB-2}$ for the analogous region of EGFR (juxtamembrane or TK-1 domain) was alone sufficient to decrease the ability of the chimeric EGFR/erbB-$2^{TK1}$ receptor to phosphorylate eps15.

These differences were not due to different levels of expression of the chimeric molecules and wild type EGFR in NIH-3T3 transfectants, as shown by $^{125}$I-EGF binding experiments, nor to differences in the levels of eps15 expressed in the various transfectants. In addition, it has previously been shown that all of the employed chimerae possess in vivo tyrosine kinase activity as demonstrated by efficient autophosphorylation and competence at phosphorylating intracellular substrates, including PLC-γ (Fazioli et al., *Mol. Cell. Biol.* 11: 2040–2048 (1991); Segatto et al., *Mol. Cell. Biol.* 11: 3191–3202 (1991); Di Fiore et al., *Mol. Cell. Biol.* 10: 2749–2756 (1990)), and ability to deliver sizable mitogenic signals in NIH-3T3 cells (Di Fiore et al., *Mol. Cell. Biol.* 10: 2749–2756 (1990); Segatto et al., *Mol. Cell. Biol.* 11: 3191–3202 (1991); Fazioli et al., *Mol. Cell. Biol.* 11: 2040–2048 (1991); Di Fiore et al., *Science* 248: 79–83 (1990)). It was concluded, therefore, that the juxtamembrane (or TK-1) region of the EGFR contains the determinants responsible for efficient phosphorylation of eps15.

The mechanisms by which the EGFR phosphorylates the eps15 gene product remain to be established. In repeated experiments, co-immunoprecipitation of these two proteins was not detected. This indicates either phosphorylation by a second kinase, activated by the EGFR, or disruption of the EGFR/eps15 complex even under the mild lysis conditions employed in the co-immunoprecipitation experiments. It is widely accepted now that detergent-resistant interactions between TKRs and some of their substrates are made possible by binding of specialized regions of substrate molecules, known as SH2 domains, to phosphotyrosine motifs present in TKRs (Koch et al., *Science* 252: 668–674 (1991)). To this regard, it is noted that the eps15 cDNA describes the synthesis of a protein lacking SH2 domains. The SH2/pTyr interactions, however, may not be the sole ones responsible for receptor/substrate interactions, and others, possibly of a weaker type, night exist. There is now evidence that purified EGFR can directly phosphorylate bacterially expressed $p142^{eps15}$ in vitro assays (W. Wong and P. P. Di Fiore, unpublished observations).

J. Detection of Altered Mitogenic Signal Transduction

The eps15 of the present invention is also valuable in detection of altered mitogenic signal transduction. Such altered signal transduction can be ascertained by measurement of eps15 levels in vivo or in vitro using the immunoassays discussed above. Alternatively, altered forms of eps15 can be detected by using at least a portion of the DNA encoding eps15 as a probe to isolate the DNA encoding a possibly altered form of eps15. Techniques of the type disclosed in Examples 2 and 3, or other conventional techniques, can then be used to sequence the isolated DNA. By comparing this sequence to the known sequence, alterations can be detected.

If an altered eps15 sequence or abnormal levels of eps15 are detected in malignant tissue, antisense therapy can be utilized in accordance with Example 11 to halt translation of the protein, or triple helix therapy in accordance with Example 12 to shut-off RNA transcription, and, thus, in both cases, to interfere with mitogenesis.

K. Increasing the Mitogenic Response of Cells

We have also discovered that the mitogenic response of cells to mitogenic factors can be enhanced by delivering eps15 to the cell in amounts greater than the natural amounts. The optimum dosage for any particular cell type can be empirically determined in a relatively straightforward manner. It is apparent that an increased dosage will have a mitogenesis-enhancing effect as demonstrated by the observation that overexpression of eps15 is sufficient to transform NIH-3T3 cells.

Particular aspects of the invention may be more readily understood by reference to the following examples, which are intended to exemplify the invention, without limiting its scope to the particular exemplified embodiments.

EXAMPLE 1

Generation of Polyclonal Antibody Against EGFR Substrates

Immunoaffinity chromatography techniques were used to isolate proteins which were tyrosine phosphorylated by EGFR, as described by Fazioli et al., *J. Biol. Chem.* 267: 5155–5161 (1992). Briefly, genetically engineered NIH-3T3 cells which overexpress EGFR (NIH-EGFR) (Fazioli et al., *Mol. Cell Biol.* 11: 2040–2048 (1991)) were maintained in DMEM (Gibco, Gaithersburg, Md. supplemented with 10% calf serum (Gibco, supra). Subconfluent cell monolayers were treated with EGF (Upstate Biotechnology, Inc. (UBI), Lake Placid, N.Y.), and lysed. EGFR was removed from the lysate using an anti-EGFR column prepared by linking anti-EGFR monoclonal antibody (Ab1, Oncogene Science, Uniondale, N.Y.) to agarose beads. The lysate was then contacted with an anti-phosphotyrosine (anti-pTyr, Oncogene Science, supra) column; the column was washed; and the bound protein was then eluted. Fractions were collected and were used to immunize two New Zealand white rabbits, yielding two polyclonal immune sera, designated 450 and 451.

EXAMPLE 2

Identification of eps15 cDNA Clone

A pool of sera 450 and 451 from Example 1 was used to screen a commercial (Clontech, Palo Alto, Calif.) λgt11 library from NIH-3T3 cells. Recombinant plaques ($10^6$) were initially screened with a 1:200 dilution of each antibody in TTBS (0.05% Tween 20 mM Tris-HCl [pH 7.5] 150 mM NaCl) containing 1% BSA. Detection was carried out with a goat anti-rabbit Ab conjugated to alkaline phosphatase by utilizing a commercial kit (Picoblue, Stratagens, La Jolla, Calif.) according to the manufacturer's specification. Analysis yielded several positive plaques; one of these clones (pl 15) contained an insert of ~1.8 kbp which was completely sequenced and had no correspondence to sequences present in the Genbank or EMBL data banks. The pl 15 insert was subcloned in the Eco RI site of pBluescript® (Stratagene, supra).

The sequence of pl 15 predicted an ORF which started in the expected frame with the β-galactosidase portion of λgt11 but contained neither an initiation nor a stop codon. It was concluded that pl 15 represented a partial cDNA encoding a novel protein, now designated eps15 (for EGFR pathway substrate #15).

EXAMPLE 3

Isolation and Sequencing of eps15 cDNA

Full length cDNA for eps15 (pCEV-eps15) was obtained by screening a mouse keratinocyte cDNA library (Miki et al., *Science* 251: 72–75 (1991)) using the pl 15 insert from Example 2 as a probe according to standard procedures (Sambrook et al., *Molecular Biology: A Laboratory Manual* (Cold Spring Harbor Laboratory Press 1989). DNA sequencing was performed by the dideoxy-termination method on both strands of the cDNA, using a commercial kit (SEQUENASE®, United States Biochemical, Cleveland, Ohio). The resulting DNA sequence is identified as SEQ ID NO:3. The 3033 bp sequence was found to contain a stop codon at position 2802–2804 followed by a 3' untranslated sequence containing a putative polyadenylation site (AATTAAA) starting at position 3014. The first in-frame ATG (position 111–113) conformed to Kozak's rules for translational initiation (Kozak M., *J. Cell Biol.* 108:229–241 (1989)) and was preceded by 110 bp of 5' untranslated sequence.

EXAMPLE 4

Preparation of Anti-eps15 Antibody and Expression of eps15 Gene Product

Polyclonal antibodies specific for the eps15 gene product were generated against a recombinant trpE fusion protein. To this end the open reading frame (ORF) of pl 15, positioned between two Eco RI sites, was cloned in frame in the Eco RI site of the pATH 11 bacterial expression vector. The recombinant fusion protein was expressed by induction with indoleacrylic acid (Koerner et al., *Methods Enzymol.* 194: 477–490 (1991)), gel purified and used to immunize New Zealand rabbits. A commercially available anti-phosphotyrosine (anti-pTyr) monoclonal antibody (Upstate Biotechnology, Lake Placid, N.Y.) was also used. Specificity of detection for anti-pTyr was controlled as described previously (Fazioli et al., *J. Biol. Chem.* 267: 5155–5161 (1992); Fazioli et al., *Mol. Cell Biol.* 11: 2040–2048 (1991), which are both incorporated by this reference).

The anti-eps15 serum specifically recognized a major species of Mr 142 kDa ($p142^{eps15}$) and a minor component of 155 kDa ($p155^{eps15}$) in NIH-EGFR cells. A second doublet of much lower intensity, migrating as 119–122 kDa, was also specifically recognized by the anti-eps15 serum. The size of the major eps15 band (142 kDa) was significantly larger than that of the deduced protein (approximately 98 kDa). This difference is not due to N-linked glycosylation, since no differences in the electrophoretic mobility of eps15 were detectable after tunycamicin treatment. In addition, in vivo transcription and translation of the pCEV-eps15 cDNA yielded a protein comigrating with authentic $p142^{eps15}$. Therefore, the discrepancy between the actual and deduced size of eps15 should be ascribed to either abnormalities in its gel migration, or to post-translational modification still occurring in a reticulocytes lysate. Analysis of sequential immunoprecipitation and immunoblotting with anti-pTyr and anti-eps15 antibodies of lysates prepared from NIH-EGFR cells, before and after in vitro EGF treatment, indicated that both p142$^{eps15}$ and p155$^{eps15}$ were phosphorylated in vitro on tyrosine following EGFR activation.

Anti-pTyr recovery of the eps15 product might be due to direct recognition of phosphotyrosil residues or to association with other pTyr-containing proteins. To distinguish between these possibilities immunoprecipitation experiments with anti-eps15 were performed, followed by immunoblot with anti-pTyr. It was found that p142$^{eps15}$ was readily detectable under these conditions in cell lysates obtained from NIH-EGFR cells triggered with EGF; p142$^{eps15}$ was not detectable in cell lysates from untreated cells. Under these same conditions, it was not easy to detect p155$^{eps15}$ in EGF-treated NIH-EGFR cells due to the presence of a superimposed background band in experiments on cell lysates from untreated cells. Nevertheless, these results established that eps15 is tyrosine phosphorylated following EGFR activation.

EXAMPLE 5

Derivation of Partial Human eps15 Sequence

The partial human eps15 sequence was obtained by the polymerase chain reaction (PCR) method using two oligonucleotides from the mouse eps15 cDNA sequence as primers to amplify the human cDNA fragment from a human cDNA library. The library used was from A101D cells (human melanoma cells, Giard et al., *J. Nat'l Cancer Institute* 51: 1417–1423 (1973)), although other readily-available libraries could be used. The library was prepared using the method of Miki et al., *Science* 251: 72–75 (1991). The two oligonucleotide PCR primers were:

1) 5' CGAGCTCGAGGTGCATCCAGCAACAG-CAGTA 2) 5' CGATATCGATTTGCTTGGGTCAGCCTCTTTA and included sequences corresponding to positions 2137–2157 and 2618–2638 of the mouse eps15 cDNA sequence (SEQ ID NO:3), respectively. A typical PCR contained 100 ng of cDNA library DNA, 5 units of Taq DNA polymerase (Boehringer Mannheim, Indianapolis, Ind.), 1 µM of each oligonucleotide primer, 200 µM dNTPs, 10 mM Tris-HCl (pH 8.3), 1.5 mM MgCl$_2$, 50 mM KCl, 0.1 mg/ml gelatin. Reactions were carried out for 35 cycles of 1.5 min at 94° C., 5 min at 50° C., and 2 min at 72° C. Reactions were then terminated with an additional 10 min at 72° C. The PCR products were purified by chroma spin+TE-400 column (Clontech, Palo Alto, Calif.), subcloned into pBluescript® II KS vector (Stratagene, La Jolla, Calif.), and sequenced by the dideoxy-termination methods on both strands using the SEQUENASE® DNA sequencing kit (USB, Cleveland, Ohio).

EXAMPLE 6

Identification of Human eps15 cDNA clone

A PCR-amplified fragment of 519 bp, acquired in accordance with Example 5, was used to screen a human cDNA library from M426 cells, although other readily available libraries could be used. Several clones were isolated and the longest cDNA (SEQ ID NO:1) was DNA- sequenced by the dideoxy-termination method, as explained in Example 3. The human eps15 clone obtained was 4165 nucleotides long and possessed an ATG at positions 21–23 which conformed to Kozak's rules for translation initiation (Kozak et al., *J. Cell. Biol.* 108: 229–241 (1989)). The clone displayed a stop codon at position 2709–2711. It was not determined whether this was a full length clone, but it encompassed the entire open reading frame of eps15, as established by comparison to the mouse cDNA.

EXAMPLE 7

Isolation of eps15 sequences from other Organisms

Two potentially complementary strategies are used to isolate and clone the eps15 gene in other species. The first strategy is essentially the same as the one used to obtain the human eps15 sequence. Briefly, two oligonucleotides from the mouse or the human eps15 sequence can be used to PCR amplify fragments of eps15 cDNA from other species. The oligonucleotides can be designed from regions of high nucleotide identity between the human and mouse sequence, in a way to increase the probability of obtaining an efficient matching of the primers with the eps15 sequences of other species. Alternatively, degenerate PCR primers can be used to amplify sequences similar to the mouse or human gene. The template for the PCR reaction can be a cDNA library from cells of another species or a cDNA obtained by reverse transcriptass (in the so called reverse transcriptase/PCR method) directly from the mRNA of another species. A second approach relies on classical low stringency hybridization of nucleic acids. In this case a probe representing the eps15 cDNA from human or mouse is hybridized, under relaxed conditions of stringency, against libraries (cDNA or genomic) prepared from cells of other species. Relaxed stringency is obtained by modifying the temperature and the ionic strength of the hybridization buffer by well known methods, in a manner designed to allow stable formation of hybrids which are not 100% matching (as expected in interspecies hybridization). The positives are then analyzed as described above (see Example 6). A complete review on low stringency hybridization is to be found in Kraus et al., *Methods in Enzymmology* 200: 546–556 (1991), which is hereby incorporated by reference.

EXAMPLE 8

Quantitative Immunoassay for eps15

It is often desirable to determine the quantity of eps15 in a sample. This can be particularly useful in clinical research, as well as in detecting abnormalities in mitogenic signal transduction in malignant tissue. Additionally, in many human tumors, tumor markers are released in the blood stream at levels which correlate with the size of the tumor and its clinical stage. Determining the levels of markers (such as eps15) in biological fluids can be advantageous in aiding the diagnostic procedures and in monitoring the effectiveness of therapy.

In one exemplary technique, anti-eps15 antibody from Example 4 is immobilized to an agarose column, as explained in Example 1. Sample is then directed through the column where eps15 in the sample is bound by the immobilized antibody. Next, a known quantity of radiolabeled anti-eps15 antibody is directed through the column. The quantity of labeled antibody which is not retained on the column is measured, and bears a relationship to the quantity of eps15 in the sample.

Another exemplary technique is liquid phase radioimmunoassay. First, a standard measurement is made by challenging a known amount of purified eps15, radiolabeled in a conventional manner, against a known amount of anti-eps15 antibody. The resulting immunocomplex is recovered by centrifugation, and the radioactivity of the centrifugate is determined. This value is used as a standard against which later measurements are compared.

Next, a sample, containing an unknown amount of eps15, is challenged against the same known amount (used in making the standard measurement) of anti-eps15 antibody. Then, the same amount of labeled eps15 used in making the standard measurement is added to the reaction mixture, followed by centrifugation and measurement of radioactivity as explained above. The decrease in the immunoprecipitated radioactivity (in comparison to the standard) is proportional to the amount of eps15 in the sample.

Of course, in addition to the foregoing exemplary methods, any of the well known conventional immunoassay methods may similarly be used.

EXAMPLE 9

Assay for Phosphorylation of eps15 by TKRs

A biological sample is assayed for TKR tyrosine kinase activity by combining the sample with known quantities of eps15 and $^{32}$P-labeled γ-ATP. The sample is then contacted with anti-eps15 from Example 4 immobilized on a column; the column is washed; and the bound eps15 is eluted with 0.1M glycine, pH 2.5. The eluant is then subjected to fractionation to separate the resulting radiolabeled eps15 from the free radioactivity in the sample using any conventional technique, such as precipitation in 5–10% trichloroacetic acid. Following fractionation, the amount of radioactivity incorporated into the eps15 is counted to measure TKR tyrosine kinase activity of the sample.

EXAMPLE 10

Alternative Assay for TKR Tyrosine Kinass Activity 100 ng of eps15 is added to 1 ml buffered cell lysate suspected of having TKR tyrosine kinase activity, together with 30 μC $^{32}$P-γATP. Following incubation, the mixture is heated to 100° C. in a solution containing sodium lauryl sulfate (SDS) and β-mercaptoethanol. Aliquots are electrophoresed on 10–15% gradient SDS polyacrylamide gels and exposed to X-Omat X-ray film to identify radioactive eps15. Cell lysate from eps15-transfected cells incubated in the presence of radiolabeled amino acids is used to confirm the location on the gel of the phosphorylated eps15.

EXAMPLE 11

Preparation and Use of Antisense Oligonucleotides

Antisense RNA molecules are known to be useful for regulating translation within the cell. Antisense RNA molecules can be produced from the sequences of the present invention. These antisense molecules can be used as therapeutic agents to regulate gene expression.

The antisense molecules are obtained from a nucleotide sequence by reversing the orientation of the coding region with regard to the promoter. Thus, the antisense RNA is complementary to the corresponding mRNA. For a review of antisense design see Green et al., *Ann. Rev Biochem.* 55: 569–597 (1986), which is hereby incorporated by reference. The antisense sequences can contain modified sugar phosphate backbones to increase stability and make them less sensitive to RNase activity. Examples of the modifications are described by Rossi et al., *Pharmocol. Ther.* 50: 245–254, (1991).

Antisense molecules are introduced into cells that express the eps15 gene. In a preferred application of this invention, the effectiveness of antisense inhibition on translation can be monitored using techniques that include, but are not limited to, antibody-mediated tests such as RIAs and ELISA, functional assays, or radiolabeling. The antisense molecule is introduced into the cells by diffusion or by transfection procedures known in the art. The molecules are introduced onto cell samples at a number of different concentrations, preferably between $1\times10^{-10}$M to $1\times10^{-4}$M. Once the minimum concentration that can adequately control translation is identified, the optimized dose is translated into a dosage suitable for use in vivo. For example, an inhibiting concentration in culture of $1\times10^{-7}$M translates into a dose of approximately 0.6 mg/kg bodyweight. Levels of oligonucleotide approaching 100 mg/kg bodyweight or higher may be possible after testing the toxicity of the oligonucleotide in laboratory animals.

The antisense molecule can be introduced into the body as a bare or naked oligonucleotide, oligonucleotide encapsulated in lipid, oligonucleotide sequence encapsidated by viral protein, or as oligonucleotide contained in an expression vector. The antisense oligonucleotide is preferably introduced into the vertebrate by injection. Alternatively, cells from the vertebrate are removed, treated with the antisense oligonucleotide, and reintroduced into the vertebrate. It is further contemplated that the antisense oligonucleotide sequence is incorporated into a ribozyme sequence to enable the antisense to bind and cleave its target. For technical applications of ribozyme and antisense oligonucleotides, see Ross et al., supra.

EXAMPLE 12

Preparation and Use of Triple Helix Probes

Triple helix oligonucleotides are used to inhibit transcription from a genome. They are particularly useful for studying alterations in cell activity as it is associated with a particular gene. The eps15 sequence or, more preferably, a portion thereof, can be used to inhibit gene expression in individuals suffering from disorders associated with the eps15 gene. Similarly, a portion of the eps15 gene sequence, or the entirety thereof, can be used to study the effect of inhibiting transcription of the gene within a cell. Traditionally, homopurine sequences were considered the most useful. However, homopyrimidine sequences can also inhibit gene expression. Thus, both types of sequences corresponding to the eps15 gene are contemplated within the scope of this invention. Homopyrimidine oligonucleotides bind to the major groove at homopurine:homopyrimidine sequences. As an example, 10-mer to 20-mer homopyrimidine sequences from the eps15 gene can be used to inhibit expression from homopurine sequences. Moreover the natural (beta) anomers of the oligonucleotide units can be replaced with alpha anomers to render the oligonucleotide more resistant to nucleases. Further, an intercalating agent such as ethidium bromide, or the like, can be attached to the 3' end of the alpha oligonucleotide to stabilize the triple helix. For information on the generation of oligonucleotides suitable for triple helix formation see Griffin et al., *Science* 245: 967–971 (1989), which is hereby incorporated by this reference.

The oligonucleotides may be prepared on an oligonucleotide synthesizer or they may be purchased commercially from a company specializing in custom oligonucleotide synthesis. The sequences are introduced into cells in culture using techniques known in the art that include but are not limited to calcium phosphate precipitation, DEAE-Dextran, electroporation, liposome-mediated transfection or native uptake. Treated cells are monitored for altered cell function. Alternatively, cells from the organism are extracted, treated with the triple helix oligonucleotide, and reimplanted into the organism.

While particular embodiments of the invention have been described in detail, it will be apparent to those skilled in the art that these embodiments are exemplary rather than limiting, and the true scope of the invention is that defined within the attached claims.

What is claimed is:

1. Isolated or purified polynucleotide operably encoding human eps15, wherein said polynucleotide comprises a sequence encoding the amino acid sequence of SEQ ID NO:2.

2. Isolated or purified polynucleotide operably encoding murine eps15, wherein said polynucleotide comprises a sequence encoding the amino acid sequence of SEQ ID NO:4.

3. Isolated or purified polynucleotide of claim 1, wherein said amino acid encoding sequence is the protein-encoding domain of SEQ ID NO:1.

4. Isolated or purified polynucleotide of claim 2, wherein said amino acid encoding sequence is the protein-encoding domain of SEQ ID NO:3.

5. Isolated or purified polynucleotide operably encoding human eps15, wherein said polynucleotide is mRNA and comprises a mRNA transcript of the DNA sequence encoding the amino acid sequence of SEQ ID NO:2.

6. Isolated or purified polynucleotide operably encoding murine eps15, wherein said polynucleotide is mRNA and comprises a mRNA transcript of the DNA sequence encoding the amino acid sequence of SEQ ID NO:4.

7. A recombinant vector comprising the polynucleotide of claim 1.

8. A recombinant vector comprising the polynucleotide of claim 2.

9. A host cell transformed with the recombinant vector of claim 7.

10. A host cell transformed with the recombinant vector of claim 8.

* * * * *